United States Patent
Wise et al.

(10) Patent No.: US 12,402,966 B2
(45) Date of Patent: Sep. 2, 2025

(54) END OF LIFE INDICATORS FOR ROBOTIC SURGICAL INSTRUMENTS

(71) Applicant: Cilag GmbH International, Zug (CH)

(72) Inventors: Austin Wise, Cincinnati, OH (US); John A. Hibner, Mason, OH (US); Shinnosuke Inoue, Daly City, CA (US); Tom Remm, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 244 days.

(21) Appl. No.: 18/190,489

(22) Filed: Mar. 27, 2023

(65) Prior Publication Data
US 2024/0325100 A1    Oct. 3, 2024

(51) Int. Cl.
*A61B 34/37*       (2016.01)
*A61B 34/00*       (2016.01)
*A61B 34/30*       (2016.01)

(52) U.S. Cl.
CPC .............. *A61B 34/37* (2016.02); *A61B 34/70* (2016.02); *A61B 2034/301* (2016.02); *A61B 2034/305* (2016.02)

(58) Field of Classification Search
CPC .............. A61B 34/30; A61B 2034/301; A61B 2090/0803; A61B 2017/00477; A61B 2034/305
See application file for complete search history.

(56) References Cited

U.S. PATENT DOCUMENTS

| 2013/0204271 A1* | 8/2013 | Brisson ................. A61B 34/30 606/130 |
| 2016/0361048 A1 | 12/2016 | Alden et al. |
| 2022/0395292 A1 | 12/2022 | Asher et al. |

FOREIGN PATENT DOCUMENTS

| CN | 114176668 A | 3/2022 |
| WO | 2021202869 A1 | 10/2021 |

OTHER PUBLICATIONS

Written Opinion and International Search Report from corresponding PCT Application No. PCT/IB2024/052884 mailed Jul. 12, 2024.

* cited by examiner

*Primary Examiner* — Nathaniel C Chukwurah
(74) *Attorney, Agent, or Firm* — Vorys, Sater, Seymour and Pease LLP

(57) ABSTRACT

A surgical tool includes a drive housing defining an indicator aperture, a drive input rotatably coupled to a bottom of the drive housing, and an indicator assembly arranged within the drive housing and actuatable to provide visual indication that the surgical tool has exhausted its useful life. The indicator assembly includes a capstan assembly operatively coupled to the drive input such that rotation of the drive input correspondingly rotates the capstan assembly, an indicator mount secured to the drive housing, and an indicator shaft extending from the indicator mount along a longitudinal axis coaxially aligned with the indicator aperture. The capstan assembly is rotated with the drive input to actuate the indicator assembly between a non-activated state, where the indicator shaft is recessed into the indicator aperture, and an activated state, where the indicator shaft extends out of the drive housing via the indicator aperture to provide the visual indication.

25 Claims, 9 Drawing Sheets

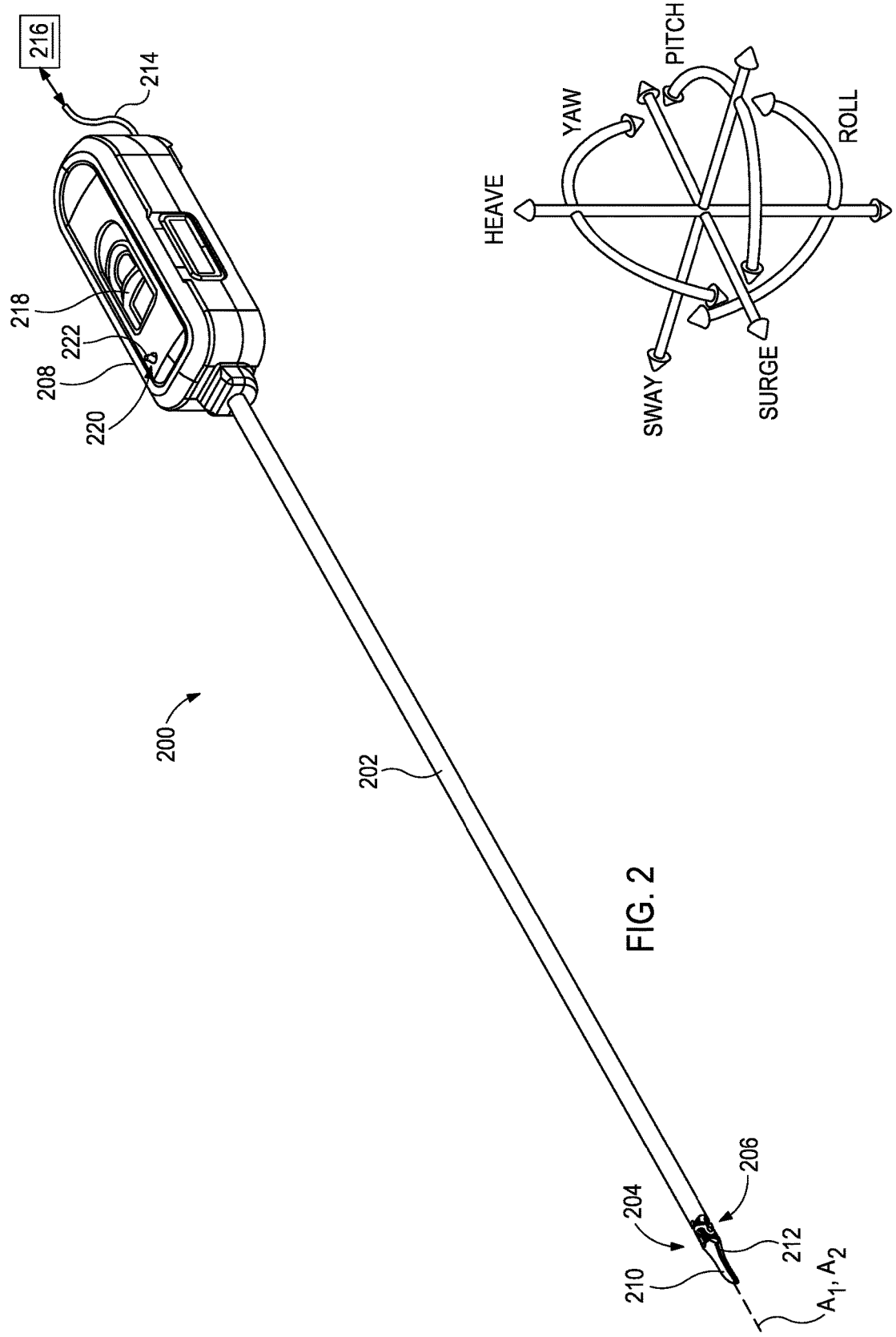

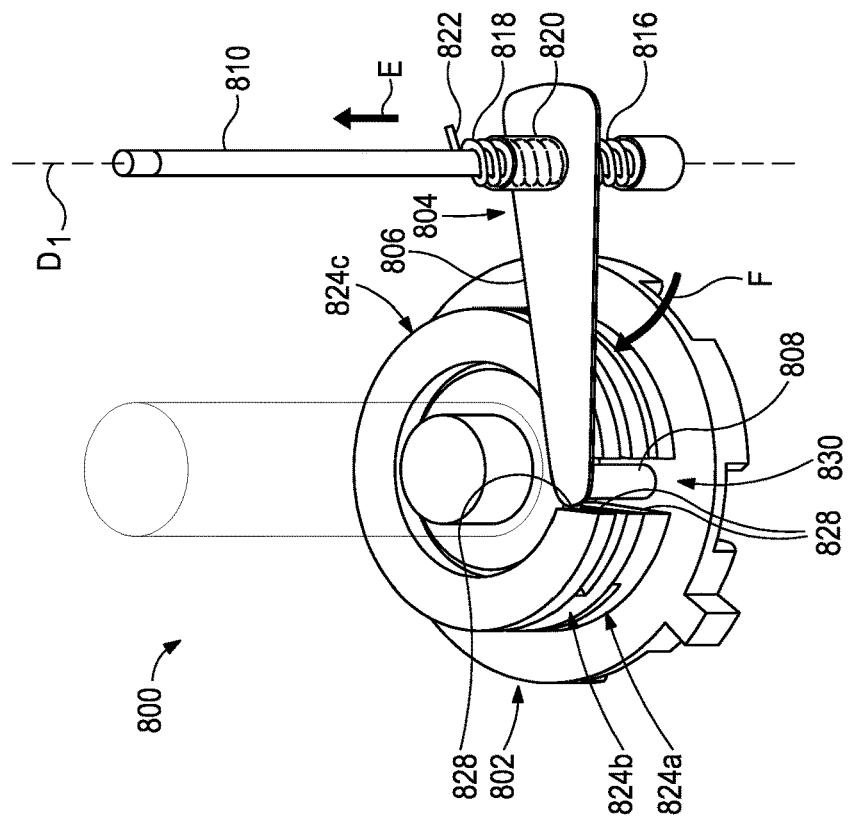
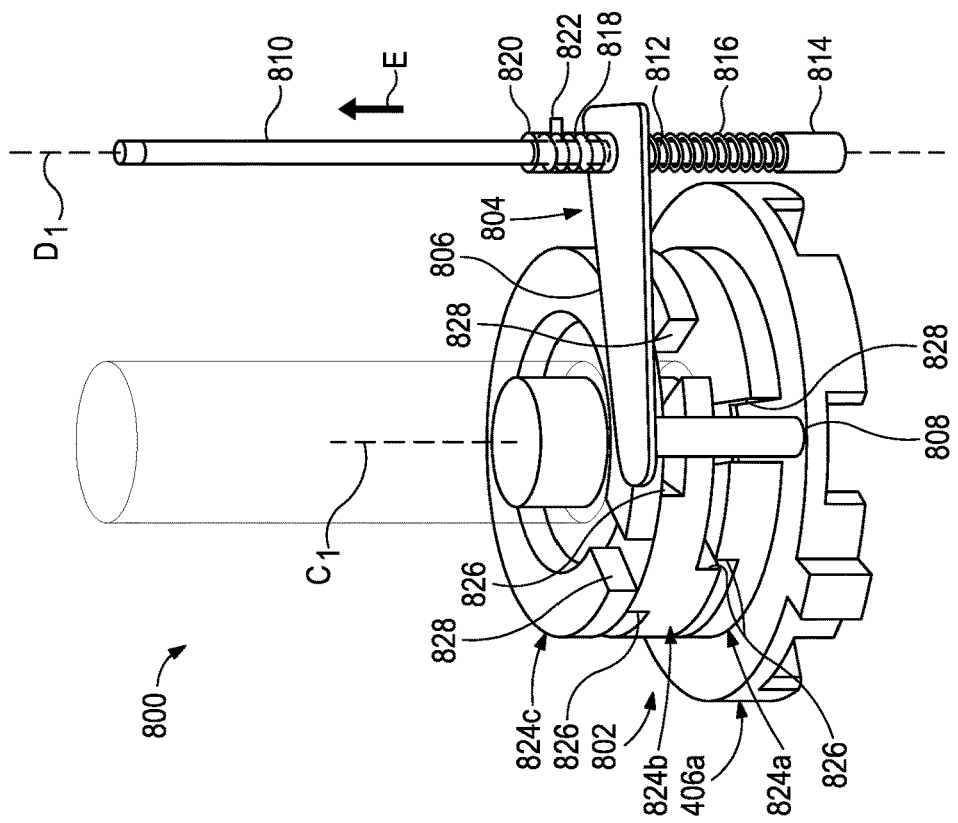
FIG. 8B
FIG. 8A

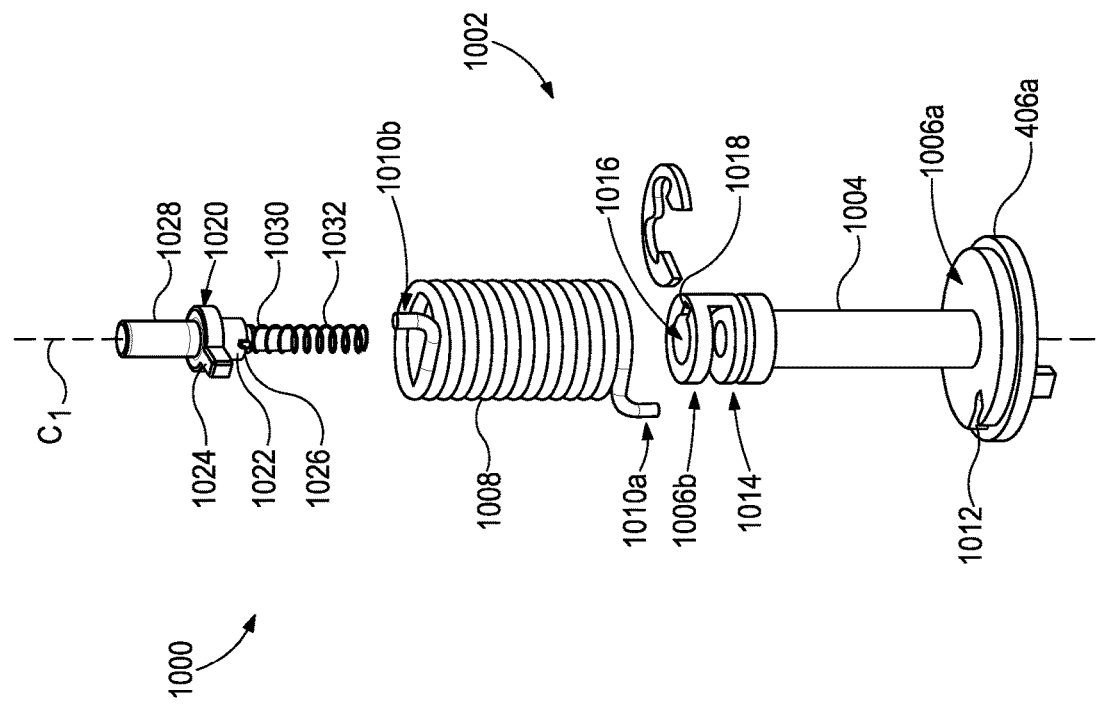
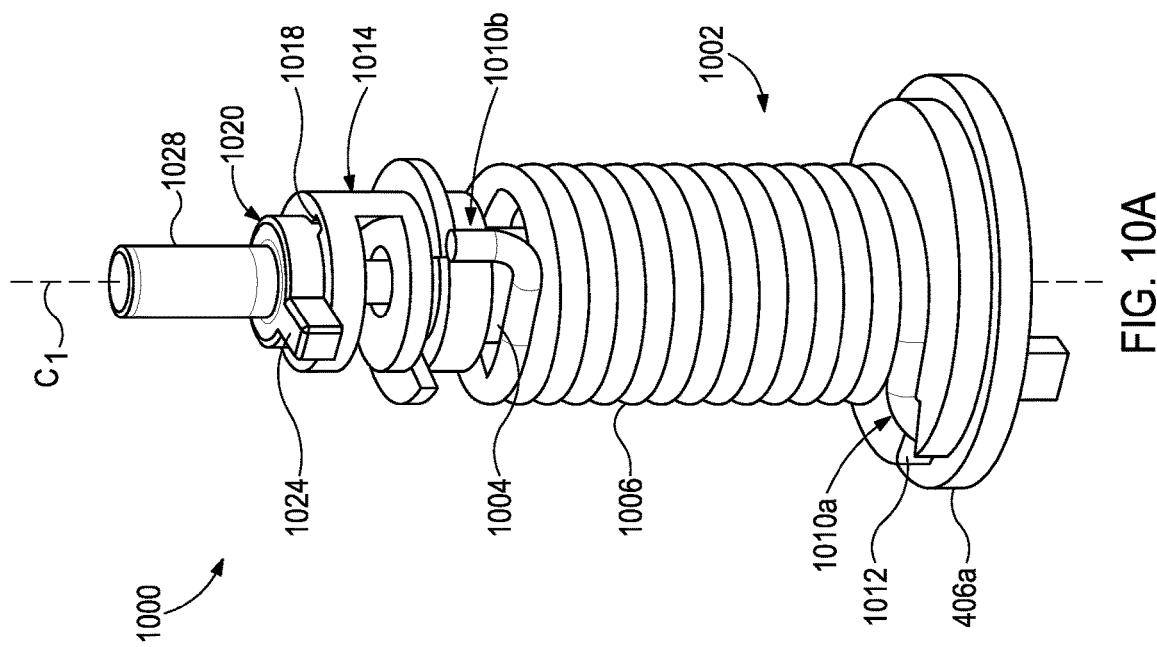

END OF LIFE INDICATORS FOR ROBOTIC SURGICAL INSTRUMENTS

BACKGROUND

Minimally invasive surgical (MIS) instruments are often preferred over traditional open surgical devices due to reduced post-operative recovery time and minimal scarring. During MIS procedures, a variety of instruments and surgical tools may be introduced into the abdominal cavity to engage and/or treat tissue in a number of ways to achieve a diagnostic or therapeutic effect. Various robotic systems have recently been developed to assist in MIS procedures by controlling such MIS instruments. A user (e.g., a surgeon) is able to remotely operate an MIS instrument's end effector by grasping and manipulating in space one or more controllers of the robotic system that communicate with a tool driver coupled to the surgical instrument. User inputs are processed by a computer system incorporated into the robotic surgical system and the tool driver responds by actuating the cable driven motion system and, more particularly, the drive cables. Moving the drive cables articulates the end effector to desired positions and configurations.

MIS instruments have limited life spans. For example, some MIS instruments are designed to expire after a predetermined number of uses or after a set period of time. In some cases, MIS instruments may include an indicator that provides indication when the useful life of the MIS instruments has been exhausted. Conventional instrument indicators are mechanically powered by one of the MIS instrument's tool drivers, which necessarily decreases overall functionality of the MIS instrument as such tool driver could instead be utilized for other tool functions. Moreover, conventional instrument indicators are not easily recognized and, consequently, sterilization workers often do not notice expired MIS instruments and are accidentally cleaned, sterilized, stored, and later sent to the operating room, despite having no useful operational life remaining. Once discovered in the operating room, personnel will be required to discard the MIS instrument and obtain a replacement. This results in frustration, procedural delay, and possible additional sedation time for the patient. Thus, it may be beneficial to provide indicators that do not utilize tool drivers and indicators that are more easily recognized.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 2 is an isometric side view of an example surgical tool that may incorporate some or all of the principles of the present disclosure.

FIG. 3 illustrates potential degrees of freedom in which the wrist of the surgical tool of FIG. 2 may be able to articulate (pivot) and translate.

FIG. 8A is an enlarged, isometric view of another example indicator assembly, according to one or more additional embodiments.

FIG. 8B is another enlarged, isometric view of the indicator assembly of FIG. 8A, according to one or more additional embodiments.

FIGS. 10A-10B are enlarged, isometric assembled and exploded views, respectively, of another example indicator assembly, according to one or more additional embodiments.

DETAILED DESCRIPTION

The present disclosure is related to robotic surgical systems and, more particularly, to tool life indicators for surgical tools.

Figure 1:
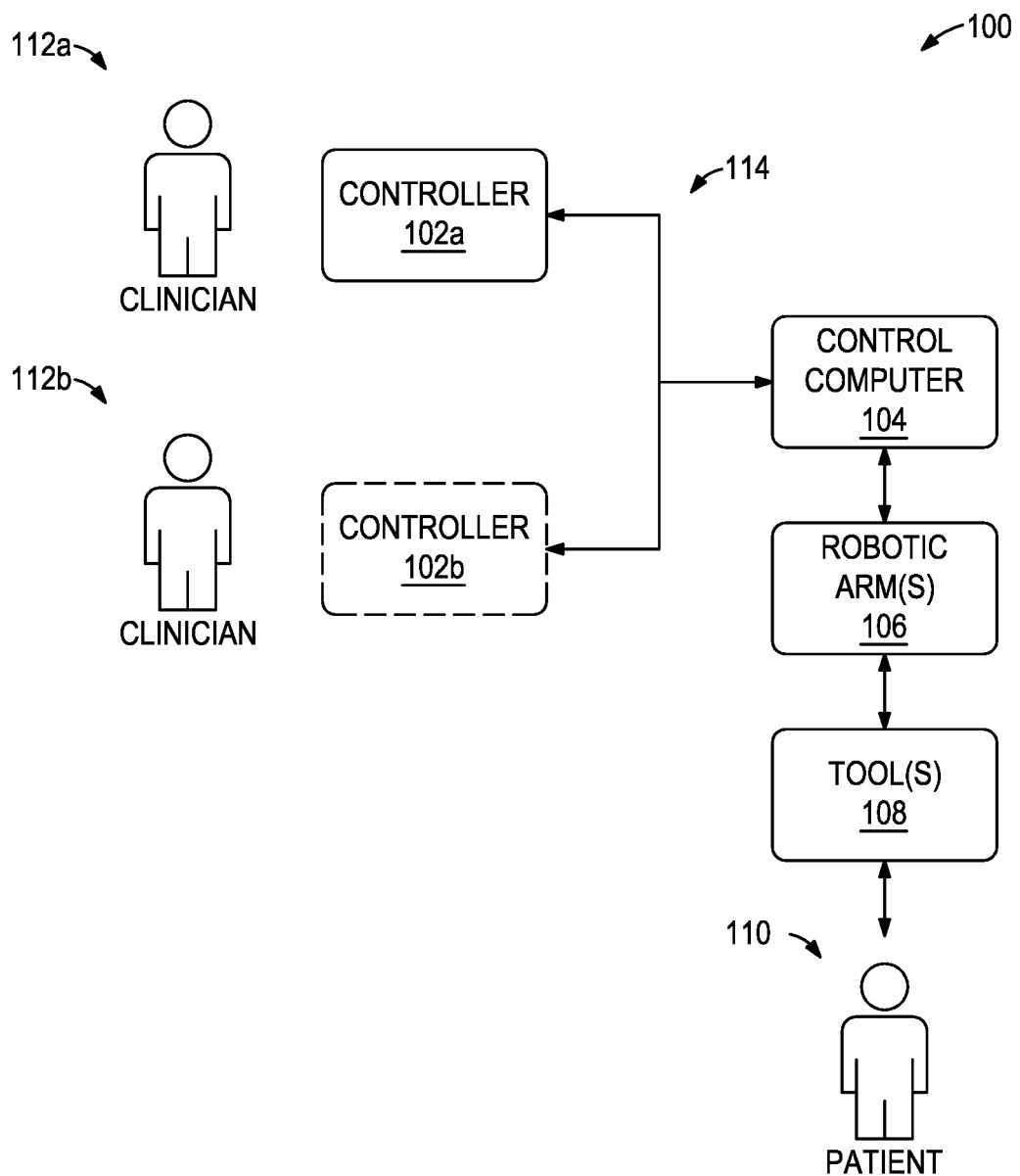
FIG. 1 is a block diagram of an example robotic surgical system that may incorporate some or all of the principles of the present disclosure.

Embodiments discussed herein describe a surgical tool that provides a visual indicator to a user, operator, or technician when the useful life of the surgical tool has been exhausted. The surgical tool can include a drive housing defining an indicator aperture, a drive input rotatably coupled to a bottom of the drive housing, and an indicator assembly arranged within the drive housing and actuatable to provide visual indication that the surgical tool has exhausted its useful life. The indicator assembly may include a capstan assembly operatively coupled to the drive input such that rotation of the drive input correspondingly rotates the capstan assembly, an indicator mount secured to the drive housing, and an indicator shaft extending from the indicator mount along a longitudinal axis coaxially aligned with the indicator aperture. The capstan assembly may be rotated with the drive input to actuate the indicator assembly between a non-activated state, where the indicator shaft is recessed into the indicator aperture, and an activated state, where the indicator shaft extends out of the drive housing via the indicator aperture to provide the visual indication FIG. 1 is a block diagram of an example robotic surgical system 100 that may incorporate some or all of the principles of the present disclosure. As illustrated, the system 100 can include at least one set of user input controllers 102a and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112a (e.g., a surgeon) from the user input controller 102a.

In some embodiments, a second set of user input controllers 102b (shown in dashed line) may be operated by a second clinician 112b to direct operation of the robotic arms 106 and tools 108 via the control computer 104 and in conjunction with the first clinician 112a. In such embodiments, for example, each clinician 112a,b may control different robotic arms 106 or, in some cases, complete control of the robotic arms 106 may be passed between the clinicians 112a,b as needed. In some embodiments, additional robotic manipulators having additional robotic arms may be utilized during surgery on the patient 110, and these additional robotic arms may be controlled by one or more of the user input controllers 102a,b.

The control computer 104 and the user input controllers 102a,b may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102a,b generally include one or more physical controllers that can be grasped by the clinicians 112a,b and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws, applying an electrical potential (current) to an electrode, or the like. The control computer 104 can also include an optional feedback meter viewable by the clinicians 112a,b via a display to provide a visual indication of various surgical instrument metrics, such as the amount of force being applied to the surgical instrument (i.e., a cutting instrument or dynamic clamping member).

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the housing 208 includes (contains) various drive inputs and mechanisms (e.g., gears, actuators, etc.) designed to control operation of various features associated with the end effector 204 (e.g., clamping, firing, cutting, rotation, articulation, etc.). In at least some embodiments, the shaft 202, and hence the end effector 204 coupled thereto, is configured to rotate about a longitudinal axis $A_1$ of the shaft 202. In such embodiments, at least one of the drive inputs included in the housing 208 is configured to control rotational movement of the shaft 202 about the longitudinal axis $A_1$.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The end effector 204 can exhibit a variety of sizes, shapes, and configurations. In the illustrated embodiment, the end effector 204 comprises a combination tissue grasper and vessel sealer that include opposing first (upper) and second (lower) jaws 210, 212 configured to move (articulate) between open and closed positions. As will be appreciated, however, the opposing jaws 210, 212 may alternatively form part of other types of end effectors such as, but not limited to, a surgical scissors, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot to articulate the end effector 204 between the open and closed positions. In other embodiments, the end effector 204 may not include opposing jaws, but may instead comprise other types of surgical end effectors such as a stapler, a cauterizer, a suction tool, an irrigation tool, and the like.

FIG. 3 illustrates the potential degrees of freedom in which the wrist 206 may be able to articulate (pivot) and thereby move the end effector 204. The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of the end effector 204 with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate actuation and articulation of the end effector 204 relative to the shaft 202. Moving (actuating) one or more of the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the housing 208. In other embodiments, the power cable 214 may be omitted and electrical power may be supplied to the surgical tool 200 via an internal power source, such as one or more batteries, capacitors, or fuel cells. In such embodiments, the surgical tool 200 may alternatively be characterized and otherwise referred to as an "electrosurgical instrument" capable of providing electrical energy to the end effector 204.

The power cable 214 may place the surgical tool 200 in electrical communication with a generator 216 that supplies energy, such as electrical energy (e.g., radio frequency energy), ultrasonic energy, microwave energy, heat energy, or any combination thereof, to the surgical tool 200 and, more particularly, to the end effector 204. Accordingly, the generator 216 may comprise a radio frequency (RF) source, an ultrasonic source, a direct current source, and/or any other suitable type of electrical energy source that may be activated independently or simultaneously.

In applications where the surgical tool 200 is configured for bipolar operation, the power cable 214 will include a supply conductor and a return conductor. Current can be supplied from the generator 216 to an active (or source) electrode located at the end effector 204 via the supply conductor, and current can flow back to the generator 216 via a return electrode located at the end effector 204 via the return conductor. In the case of a bipolar grasper with opposing jaws, for example, the jaws serve as the electrodes where the proximal end of the jaws are isolated from one another and the inner surface of the jaws (i.e., the area of the jaws that grasp tissue) apply the current in a controlled path through the tissue. In applications where the surgical tool 200 is configured for monopolar operation, the generator 216 transmits current through a supply conductor to an active electrode located at the end effector 204, and current is returned (dissipated) through a return electrode (e.g., a grounding pad) separately coupled to a patient's body.

The surgical tool 200 may further include a manual release switch 218 that may be manually actuated by a user (e.g., a surgeon) to override the cable driven system and thereby manually articulate or operate the end effector 204. The release switch 218 is movably positioned on the drive housing 208, and a user is able to manually move (slide) the release switch 218 from a disengaged position, as shown, to an engaged position. In the disengaged position, the surgical tool 200 is able to operate as normal. As the release switch 218 moves to the engaged position, however, various internal component parts of the drive housing 208 are simultaneously moved, thereby resulting in the jaws 210, 212 opening, which might prove beneficial for a variety of reasons. In some applications, for example, the release switch 218 may be moved in the event of an electrical disruption that renders the surgical tool 200 inoperable. In such applications, the user would be able to manually open the jaws 210, 212 and thereby release any grasped tissue and remove the surgical tool 200. In other applications, the release switch 218 may be actuated (enabled) to open the jaws 210, 212 in preparation for cleaning and/or sterilization of the surgical tool 200.

According to embodiments of the present disclosure, the surgical tool 200 may further include a tool end of life indicator assembly 220 that may be automatically activated (triggered) to provide a visual indication that the useful life of the surgical tool 200 has been exhausted and/or that the recommended lifespan of the surgical tool 200 has expired. The tool of life indicator assembly 220 may be alternately referred to herein as "the indicator assembly 220". Upon activation of the indicator assembly 220, the user will be visually notified that the service life of the surgical tool 200 has been exhausted and should not be cleaned for re-use but instead decommissioned (e.g., discarded).

In some examples, the surgical tool 200 may include a single tool end of life indicator assembly 220. In other examples, the surgical tool 200 may include a plurality of tool end of life indicator assemblies 220, where a first is activated after a first use, a second is activated after a second use, and so on; and activation of all of the plurality of tool end of life indicator assemblies 220 indicates that the surgical tool 200 has reached the end of its life. In at least one embodiment, the tool end of life indicator assembly 220 may provide a visual indication that the surgical tool 200 has a certain amount of life (or uses or hours of use) remaining.

Various metrics may be implemented to measure the useful life of the surgical tool 200. For example, the "useful life" may be determined by the number of procedures that the surgical tool 200 has been utilized (e.g., twenty procedures). In such embodiments, once the number of uses of the surgical tool 200 reaches a predetermined threshold, the indicator assembly 220 may be activated to visually inform the user. Alternatively, the "useful life" may be determined by the number of hours that the surgical tool 200 has been utilized, the number of articulations or movements that the surgical tool 200 has made, or any combination thereof. The indicator assembly 220 may provide a visually perceivable indication that the surgical tool 200 has exhausted its useful life or is expired, and/or that the surgical tool 200 has a certain amount of life (e.g., uses, hours of use, etc.) remaining.

As described in more detail below, the tool end of life indicator assembly 220 may include a mechanically actuated indicator button or shaft 222 that becomes visible (exposed) once the useful life of the surgical tool 200 has been exhausted or reached. In one or more embodiments, as illustrated, the indicator assembly 220 may be located on the drive housing 208, such as on a top surface of the drive housing 208. The indicator assembly 220, however, may be located at any location on the surgical tool 200 that sufficiently enables a user to visually notice the indicator shaft 222. During normal operation of the surgical tool 200, and before reaching the predetermined useful life threshold, the indicator shaft 222 may be recessed into the interior of the drive housing 208 and otherwise not visible. Once it is determined that the useful life of the surgical tool 200 has been exhausted, however, the indicator assembly 220 may be actuated (activated), which results in the indicator shaft 222 extending (protruding) a short distance out of the drive housing 208 to provide a visual indication to the user. The indicator assembly 220 is shown in FIG. 2 with the indicator shaft 222 in the activated state.

Figure 4:
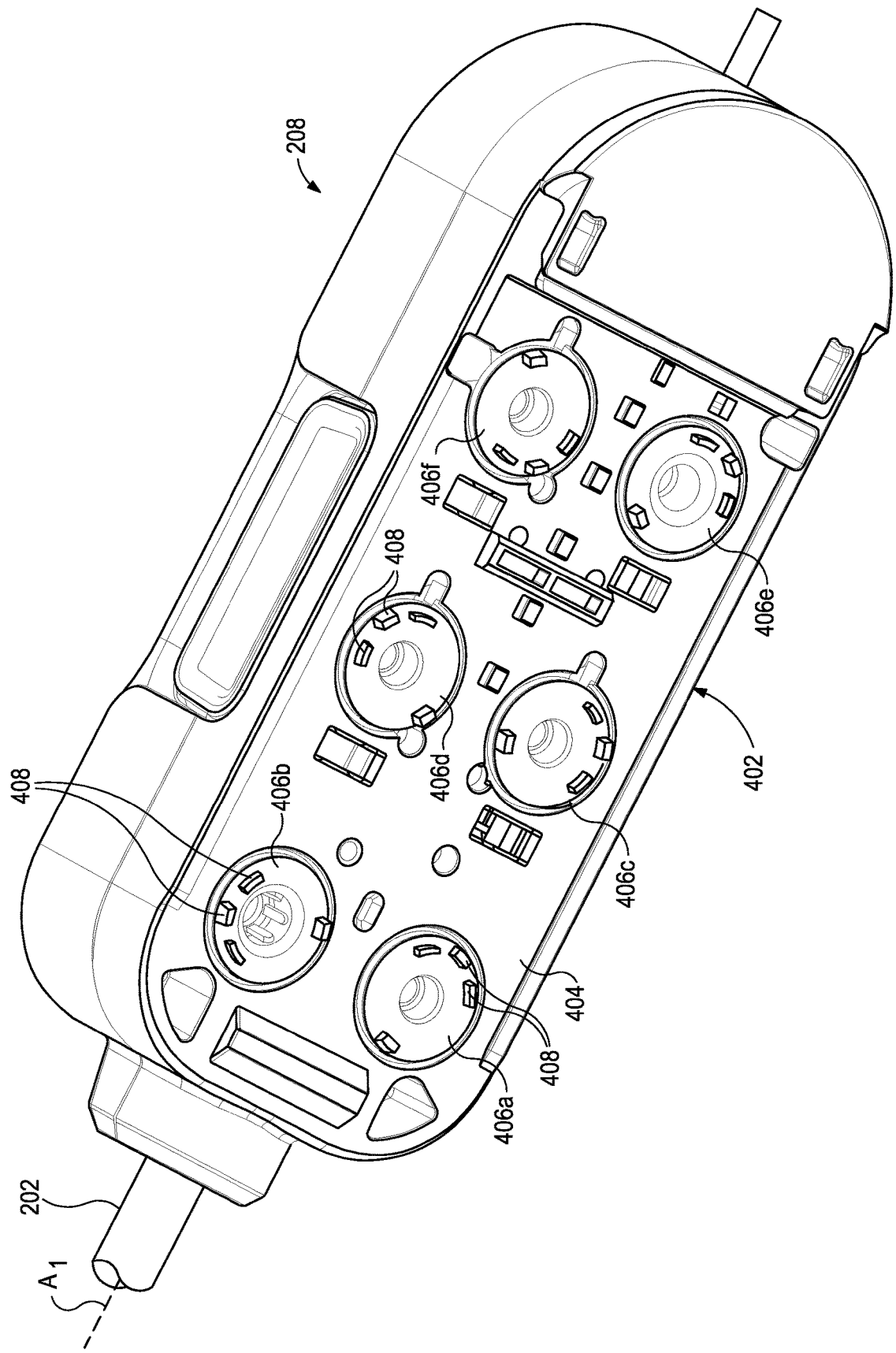
FIG. 4 is a bottom view of the drive housing of FIG. 2, according to one or more embodiments.

FIG. 4 is a bottom view of the drive housing 208, according to one or more embodiments. As illustrated, the drive housing 208 may include a tool mounting portion 402 used to operatively couple the drive housing 208 to a tool driver of a robotic manipulator. The tool mounting portion 402 may releasably couple the drive housing 208 to a tool driver in a variety of ways, such as by clamping thereto, clipping thereto, or slidably mating therewith. In some embodiments, the tool mounting portion 402 may include an array of electrical connecting pins, which may be coupled to an electrical connection on the mounting surface of the tool driver. While the tool mounting portion 402 is described herein with reference to mechanical, electrical, and magnetic coupling elements, it should be understood that a wide variety of telemetry modalities might be used, including infrared, inductive coupling, or the like.

The tool mounting portion 402 includes and otherwise provides an interface 404 configured to mechanically, magnetically, and/or electrically couple the drive housing 208 to the tool driver. As illustrated, the interface 404 includes and supports a plurality of drive inputs, shown as drive inputs 406a, 406b, 406c, 406d, 406e, and 406f. Each drive input 406a-f comprises a rotatable disc configured to align with and couple to a corresponding actuator or "drive output" of a tool driver, such that rotation (actuation) of a given drive output drives (rotates) a corresponding one of the drive inputs 406a-f. Each drive input 406a-f may provide or define one or more surface features 508 configured to align with mating surface features provided on the corresponding drive output. The surface features 508 can include, for example, various protrusions and/or indentations that facilitate a mating engagement. In some embodiments, some or all of the drive inputs 406a-f may include one surface feature 508 that is positioned closer to an axis of rotation of the associated drive input 406a-f than the other surface feature(s) 508. This may help to ensure positive angular alignment of each drive input 406a-f.

Actuation of the first drive input 406a may be configured to control actuation of the tool end of life indicator assembly 220 (FIG. 2). In some embodiments, actuating the first drive input 406a may not only control actuation of the indicator assembly 220, as described below, but may also control actuation of another feature or operation for the surgical tool 200 (FIG. 2). In other embodiments, however, actuating the first drive input 406a may solely control actuation of the indicator assembly 220, without departing from the scope of the disclosure.

Actuation of the second drive input 406b may be configured to control rotation of the shaft 202 about its longitudinal axis $A_1$. The shaft 202 may be rotated clockwise or counter-clockwise depending on the rotational actuation of the second drive input 406b. In some embodiments, actuation of the second, third, fourth, and fifth drive inputs 406b-e may be configured to operate movement (axial translation) of drive cables that form part of a cable driven motion system, which results in the actuation of the wrist 106 (FIG. 4) and/or articulation (operation) of the end effector 204 (FIG. 4). In some embodiments, actuation of the sixth drive input 406f may be configured to advance and retract a drive rod, and thereby correspondingly advance or retract a knife at the end effector 204. Each of the drive inputs 406a-f may be actuated based on user inputs communicated to the tool driver coupled to the interface 404, and the user inputs may be received via a computer system incorporated into the robotic surgical system.

The drive housing 208 may house electronics that store unique identification data for the surgical tool 200 (FIG. 2). Upon mounting the drive housing 208 to a tool driver of the robotic surgical system 100 (FIG. 1), the system 100 may be able to identify the type of tool and/or the specific tool utilized in a particular operation based on the unique identification data. In addition, the electronics of the surgical tool 200 may store the useful life of the surgical tool 200 (e.g., the use count), and the useful life of the surgical tool 200 may be determined by logic stored on one or more components of the robotic surgical system 100. Moreover, the surgical system 100 may store information related to a particular surgical tool 200, and then access and utilize that stored information when it recognizes that the particular surgical tool 200 is being utilized. For example, the robotic surgical system 100 may recognize that the surgical tool 200 has been installed in the robotic manipulator and then access its remaining useful life that was previously calculated, so that such useful tool life may be updated as needed following the particular operation in which the surgical tool 200 is being utilized.

In some embodiments, the surgical tool 200 (FIG. 2) may wirelessly communicate with the robotic surgical system 100 (FIG. 1). In particular, the robotic surgical system 100 may utilize NFC protocols to identify or authenticate the surgical tool 200 or to associate the surgical tool 200 with stored data related to the surgical tool 200. In at least some embodiments, the surgical tool 200 includes a tag that may be read remotely and wirelessly, without physical contact, when excited with energy emitted from the robotic manipulator. The tag includes an integrated circuit (or chip) that stores and processes information and modulates and demodulates signals (i.e., radio frequency or "RF" signals) and an antenna that receives and transmits the signal. The tag may include a battery and periodically self-activate to transmit a signal, or may include a battery but activate to transmit a signal when in the presence of the robotic manipulator (or other reader device), or may not include a battery and activate to send a signal when excited by the robotic manipulator (or other reader device). The tag may be read-only, having information assigned thereon, or may be read/write, where information may be written into the tag one or more times. In these examples, the robotic manipulator (or reader device) transmits an encoded radio signal to interrogate the tag within the surgical tool 200. The tag receives the encoded radio signal and responds by sending the identification and/or other information stored in the integrated circuit (e.g., serial number, use count, usage time, manufacture date, expiration date, etc.) to the robotic manipulator so that it may be analyzed by the robotic surgical system 100. Accordingly, the robotic surgical system 100 may be able to differentiate between a variety of surgical tools as the tags of each surgical tool will include unique identification data.

Figure 5A:
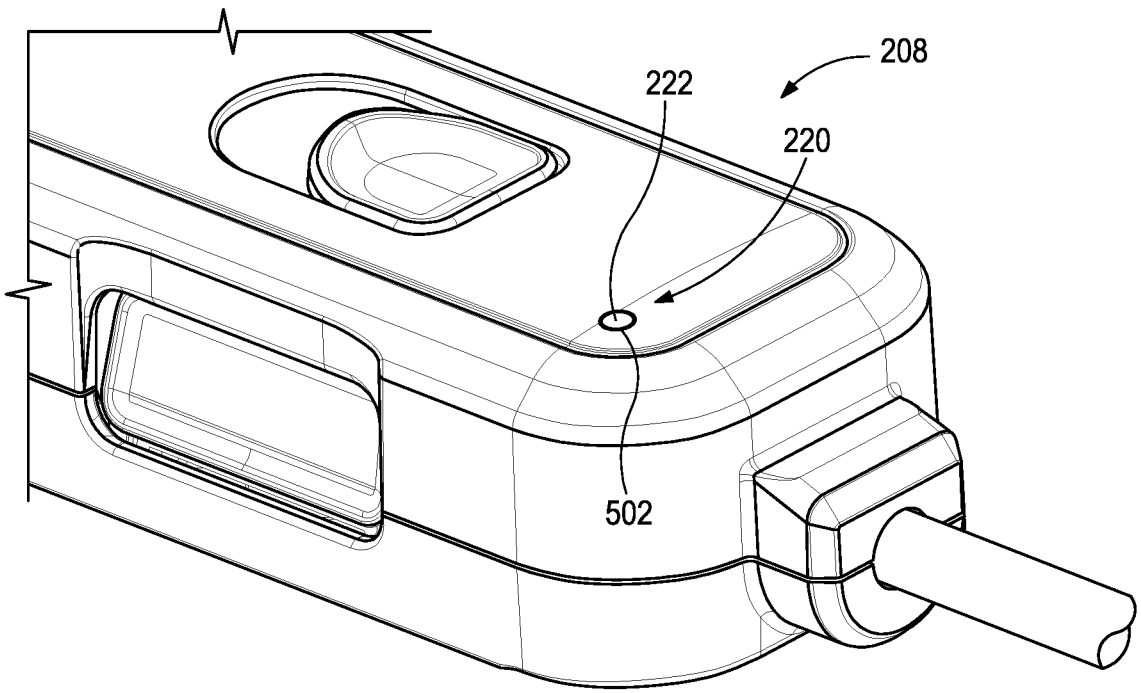
FIGS. 5A and 5B are enlarged isometric views of the drive housing of FIG. 2, according to one or more embodiments.
Figure 5B:
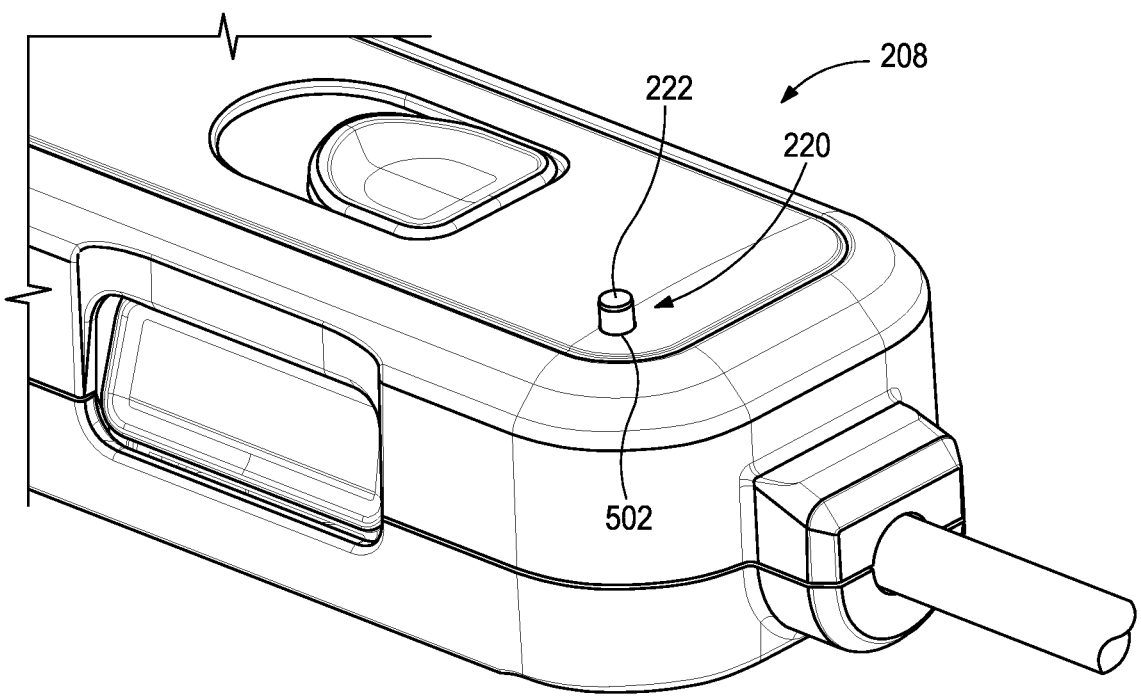

FIGS. 5A and 5B are enlarged isometric views of the drive housing 208, according to one or more embodiments. FIGS. 5A-5B also depict example actuation of the tool end of life indicator assembly 220, which includes the indicator shaft 222. In FIG. 5A, the indicator assembly 220 is in a first or "non-activated" state, and thus the indicator shaft 222 is not readily perceivable. However, in FIG. 5B, the indicator assembly 220 is transitioned to a second or "activated" state, and the indicator shaft 222 extends out of the drive housing 208 a short distance and is readily perceivable by an operator. The remaining portions of the indicator assembly 220 are housed within the drive housing 208, and various embodiments of the indicator assembly 220 will be discussed below.

When the indicator assembly 220 is in the non-activated state, as shown in FIG. 5A, the indicator shaft 222 is substantially or entirely received within the drive housing 208, such that the indicator shaft 222 is mostly or fully occluded from the view of an operator or user. In contrast, when the indicator assembly 220 is transitioned to the activated state, as shown in FIG. 5B, the indicator shaft 222 is moved such that the top or upper end of the indicator shaft 222 protrudes (extends) a short distance out of the drive housing 208 via an indicator aperture 502 defined in the drive housing 208. When the indicator shaft 222 protrudes out of the drive housing 208 via the indicator aperture 502, this provides a positive, visual indication that the surgical tool 200 (FIG. 2) has exhausted its useful life, and appropriate action should be taken.

In some embodiments, the upper end or top of the indicator shaft 222 may be painted or otherwise include or exhibit a bright color (e.g., red), which may be easily perceivable by a user when transitioned to the activated state. In at least one embodiment, the indicator shaft 222 may include a light (e.g., a light-emitting diode or "LED") that is triggered to emit light (shine) when the indicator assembly 220 transitions to the activated state. In some embodiments, the indicator assembly 220 may be configured and otherwise designed such the indicator shaft 222 cannot be advanced back into the drive housing 208 without disassembling the entire drive housing 208.

Figure 6:
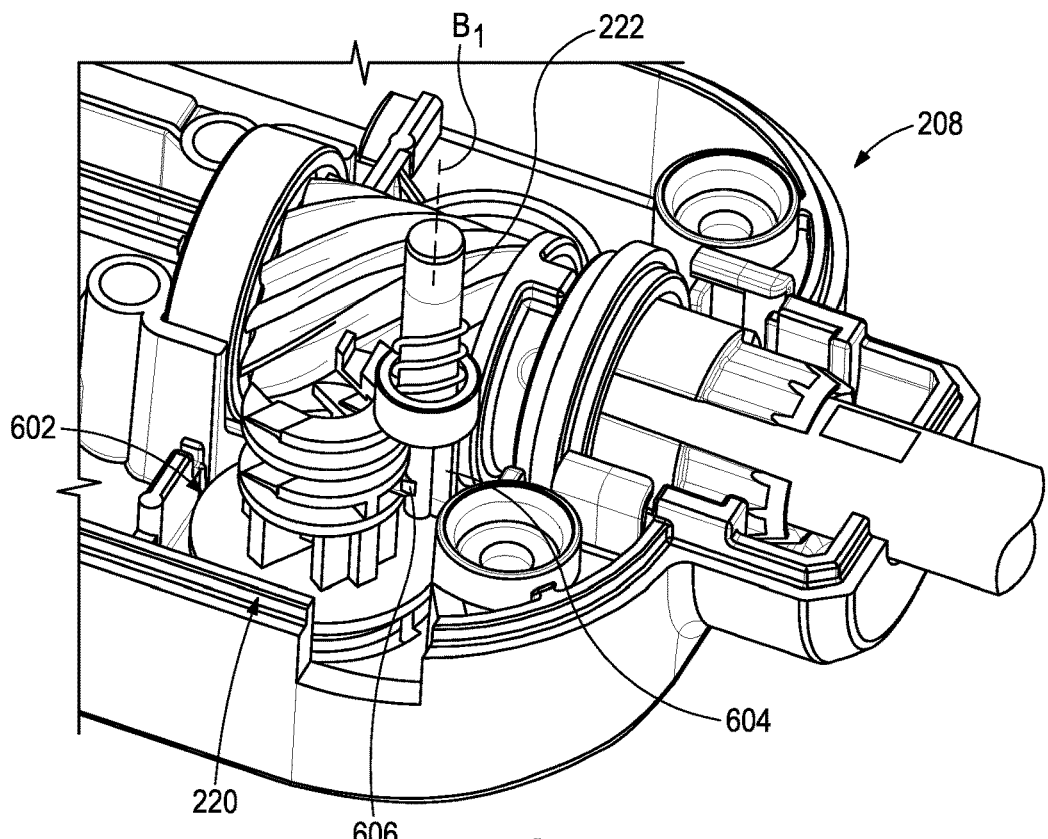
FIG. 6 is an enlarged, exposed view of the interior of the drive housing, according to one or more embodiments.

FIG. 6 is an enlarged, exposed view of a portion of the interior of the drive housing 208, according to one or more embodiments. Several component parts that would otherwise be contained within the drive housing 208 are not shown in FIG. 6 to enable discussion of the depicted component parts. As illustrated, the drive housing 208 houses and otherwise contains the indicator assembly 220. FIG. 6 depicts one example of the indicator assembly 220, and other designs or configurations of the indicator assembly 220 will be provided below.

In the illustrated embodiment, the indicator assembly 220 includes a capstan assembly 602 operatively coupled to or extending from the first drive input 406a (FIG. 4) such that actuation of the first drive input 406a results in rotation of the capstan assembly 602. The indicator assembly 220 further includes an indicator mount 604 mounted to the drive housing 208 in a manner that allows the indicator mount 604 to move (translate) up and down along a longitudinal axis $B_1$ relative to the capstan assembly 602 as the capstan assembly 602 rotates. A follower 606 (partially occluded) extends laterally from the indicator mount 604 and is configured to slidingly engage various surfaces and ramps of the capstan assembly 602, which urges the indicator mount 604 to move vertically (up and down) along the longitudinal axis $B_1$.

The indicator shaft 222 may form part of or otherwise extend from the indicator mount 604 such that as the indicator mount 604 translates (moves) along the longitudinal axis $B_1$, the indicator shaft 222 correspondingly moves in the same axial direction along the longitudinal axis $B_1$. The indicator mount 604 and the indicator shaft 222 are constrained within the drive housing 208 to movement along the longitudinal axis $B_1$, which may be coaxially aligned with the indicator aperture 502 (FIGS. 5A-5B) defined in the drive housing 208. Consequently, as the indicator mount 604 moves along the longitudinal axis $B_1$, the indicator shaft 222 is simultaneously moved toward or away from the indicator aperture 502, depending on the operation of the indicator mount 604.

The indicator assembly 220 may further include a coil spring 608 that extends about a portion of the indicator shaft 222. The bottom of the coil spring 608 may engage or be mounted to the indicator mount 604, and the top of the coil spring 608 may engage a static portion (not shown) of the drive housing 208. Consequently, as the follower 606 slidingly engages the surfaces and the ramps of the capstan assembly 602 and thereby urges the indicator mount 604 to move up and along the longitudinal axis $B_1$, the coil spring 608 will progressively compress and build spring force. In some embodiments, for example, the top of the coil spring 608 may engage the bottom internal surface of the drive housing 208 at or near the indicator aperture 502 (FIGS. 5A-5B). In other embodiments, however, the top of the coil spring 608 may engage another structure arranged within the drive housing 208, such as a chassis or another stationary surface mounted within or forming part of the drive housing 208.

Figure 7A:
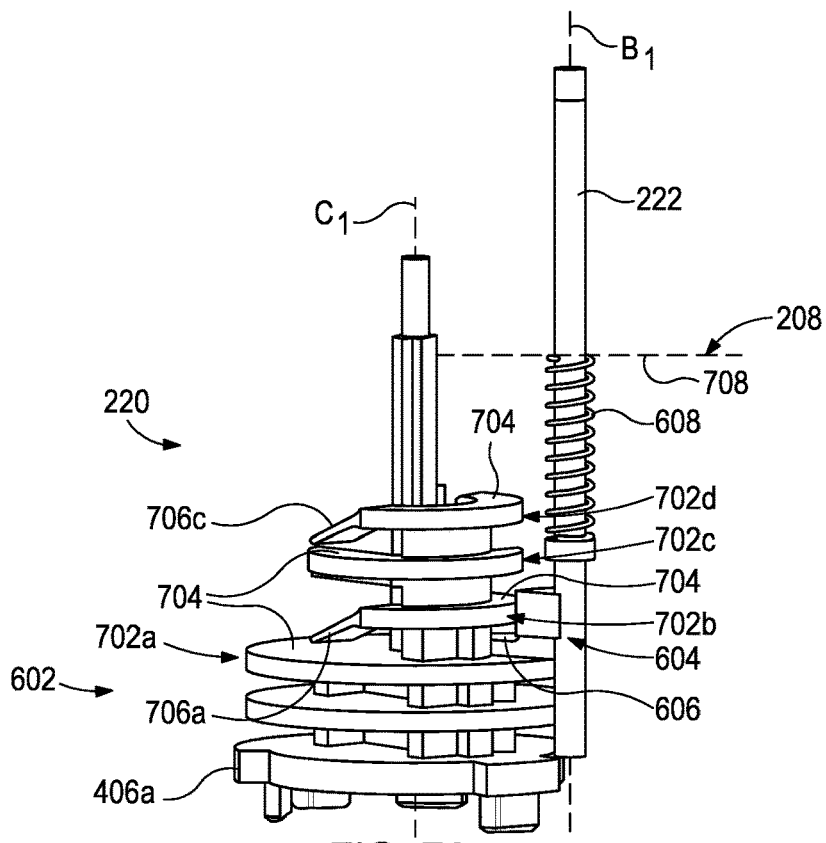
FIG. 7A is an isometric view of the indicator assembly 220 of FIG. 6, according to one or more embodiments.

FIG. 7A is an enlarged, isometric view of the indicator assembly 220 of FIG. 6, according to one or more embodiments. As illustrated, the capstan assembly 602 either forms part of or extends from the first drive input 406a, and is rotatable about a central axis $C_1$ as the first drive input 406a is rotated. Moreover, the capstan assembly 602 may include a plurality of structural levels, shown as a first structural level 702a, a second structural level 702b, a third structural level 702c, and a fourth structural level 702d. The structural levels 702a-d are axially offset from each other along the central axis $C_1$, and each structural level 702a-d includes a planar surface 704 that is parallel to the planar surfaces 704 of the other structural levels 702a-d. During actuation of the indicator assembly 220, the capstan assembly 602 rotates and the follower 606 slidingly engages the planar surfaces 704. While four structural levels 702a-d are shown, the capstan assembly 602 may include more or less than four.

The indicator assembly 220 may further include a plurality of ramps, shown as a first ramp 706a, a second ramp 706b (occluded), and third ramp 706c. Each ramp 706a-c provides a means for the follower 606 to transition vertically between vertically adjacent structural levels 702a-d and their corresponding planar surfaces 704. More specifically, the first ramp 706a provides a vertical transition from the first structural level 702a to the second structural level 702b, the second ramp 706b provides a vertical transition from the second structural level 702b to the third structural level 702c, and the third ramp 706c provides a vertical transition from the third structural level 702c to the fourth structural level 702d.

As the capstan assembly 602 is rotated in a predetermined and precise rotational sequence, the follower 606 may be able to progressively and sequentially engage each structural level 702a-d by engaging and sliding (riding) up each ramp 706a-c. As the follower 606 transitions to each level 702a-d, the indicator mount 604 and the indicator shaft 222 will correspondingly move vertically along the longitudinal axis $B_1$. Moreover, as the indicator shaft 222 moves upwards along the longitudinal axis $B_1$, the coil spring 608 will progressively be compressed against the underside (bottom) of a portion 708 of the drive housing 208 (shown as a dashed line in FIG. 7A) and thereby build spring force.

Figure 7C:
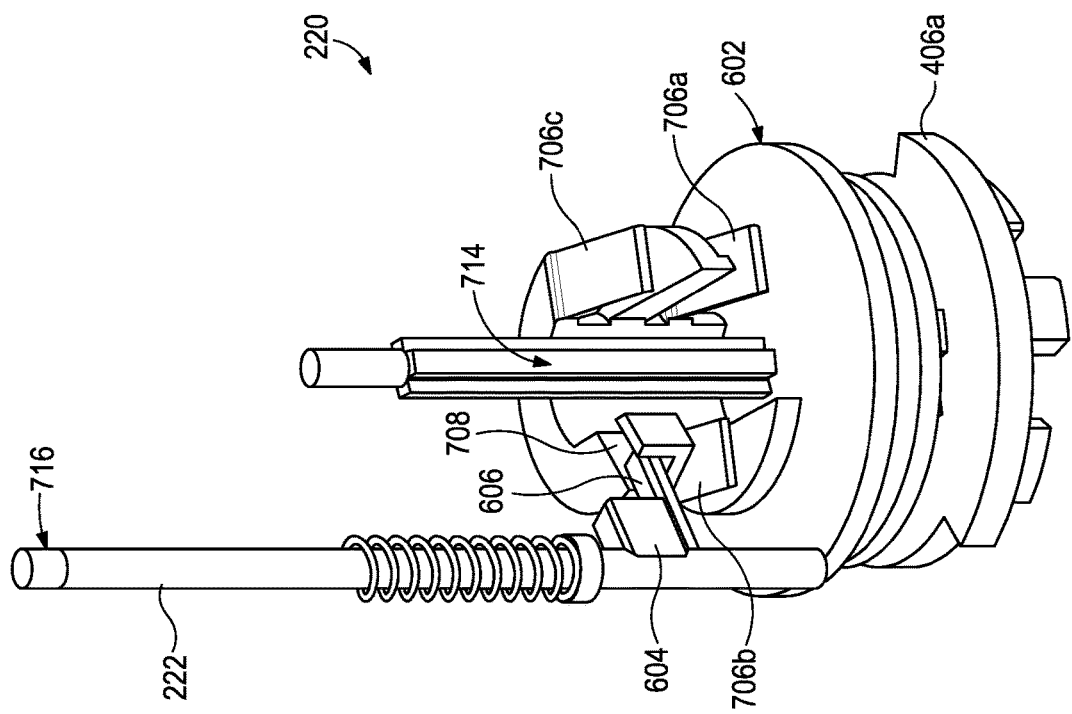
FIG. 7C is another enlarged, isometric view of the indicator assembly of FIG. 7A, according to one or more embodiments.
Figure 7B:
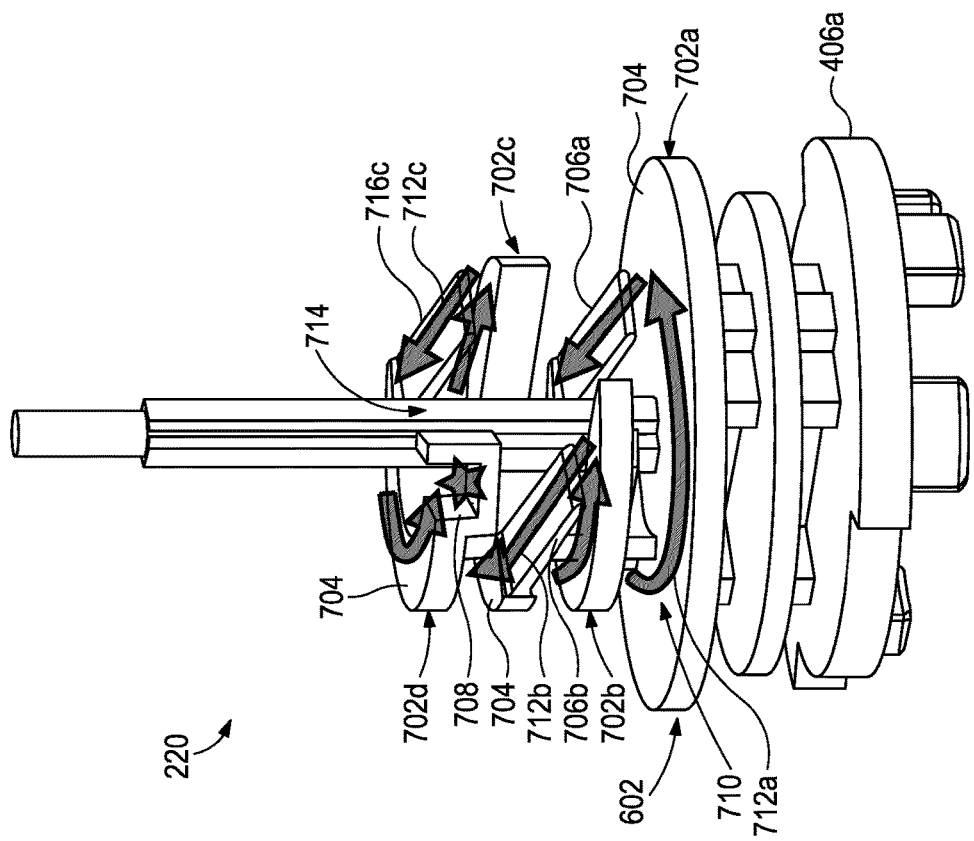
FIG. 7B is an enlarged view of the indicator assembly of FIG. 7A illustrating an example actuation pathway, according to one or more embodiments.

FIG. 7B is an enlarged view of the indicator assembly 220 of FIG. 7A illustrating an example actuation pathway 710 that the follower 606 (FIG. 7A) must traverse to properly actuate the indicator assembly 220, according to one or more embodiments. To fully actuate the indicator assembly 220, and thereby transition the indicator shaft 222 (FIGS. 7A and 7C) to the activated state, the follower 606 must precisely traverse the actuation pathway 710 up each ramp 706a-c and to each structural level 706a-d. The actuation pathway 710 terminates at a trough or pocket 708 defined by the indicator assembly 220 at the top-most, fourth structural level 706d.

The indicator assembly 220 will technically be transitioned to the activated state once the follower 606 reaches the fourth structural level 702d, but will not be fully actuated until the follower 606 reaches the pocket 708. More specifically, once the follower 606 reaches the fourth structural level 702d, the top or upper end of the indicator shaft 222 will protrude (extend) a short distance out of the drive housing 208 (FIGS. 5A-5B) to provide a positive, visual indication that the surgical tool 200 (FIG. 2) has exhausted its useful life. However, the indicator assembly 220 will be fully actuated once the follower 606 traverses the planar surface 704 of the fourth structural level 702d and is ultimately received within the pocket 708. Once the follower 606 is received within the pocket 708, the capstan assembly 602 will be prevented from further rotation in either angular direction, thereby preventing the indicator assembly 220 from returning to the non-activated state.

The follower 606 will be able to traverse the actuation pathway 710 (shown as a plurality of arrows), and thereby transition the indicator assembly 220 to the activated state, by rotating the capstan assembly 602 in a predetermined rotational sequence comprising a precise combination of clockwise and counter-clockwise rotations. The combination of precise rotational movements required to transition the indicator assembly 220 to the activated state may be sufficiently complex such that inadvertently matching the predetermined rotational sequence could only be accomplished in extremely rare circumstances.

Rotation of the capstan assembly 602 will be dictated by actuation of the first drive input 406a. As mentioned above, the drive inputs, including the first drive input 406a, are configured to align with and couple to a corresponding actuator or "drive output" of a tool driver, and rotation (actuation) of a given drive output drives (rotates) the corresponding drive input. According to embodiments of the present disclosure, once the predetermined operational threshold of the surgical tool 200 (FIG. 2) has been reached, the robotic manipulator of the tool driver may be operated to actuate the first drive input 406a in the predetermined rotational sequence, and thereby transition the indicator assembly 220 to the activated state. Accordingly, the precise combination of clockwise and counter-clockwise rotations may be known and programmed into the control computer 104 (FIG. 1) used to operate the robotic manipulator.

In the illustrated embodiment, the predetermined rotational sequence for the actuation pathway 710 includes rotating the first drive input 406a, and therefore the capstan assembly 602, in a first angular direction (e.g., counter-clockwise) for a first predetermined angular magnitude 712a. As shown in FIG. 7B, rotating the capstan assembly 602 in the first angular direction for the first predetermined angular magnitude 712a may allow the follower 606 (FIGS. 7A and 7C) to traverse the planar surface 704 of the first structural level 702a, engage and ride up the first ramp 706a, and traverse at least a portion of the planar surface 704 of the second structural level 702b.

After rotating for the first predetermined angular magnitude 712a, the predetermined rotational sequence may then include changing angular direction and rotating the first drive input 406a, and therefore the capstan assembly 602, in a second angular direction (e.g., clockwise) for a second predetermined angular magnitude 712b. Rotating the capstan assembly 602 in the second angular direction for the second angular magnitude 712b may allow the follower 606 to engage and ride up the second ramp 706b, and subsequently traverse at least a portion of the planar surface 704 of the third structural level 702c.

The predetermined rotational sequence may then include changing angular direction again and rotating first drive input 406a, and therefore the capstan assembly 602, in the first angular direction (e.g., counter-clockwise) for a third predetermined angular magnitude 712c. Rotating the capstan assembly 602 in the first angular direction for the third angular magnitude 712c may allow the follower 606 to engage and ride up the third ramp 706c, and subsequently traverse at least a portion of the planar surface 704 of the third structural level 702d. Rotating the capstan assembly 602 in the first angular direction for the third angular magnitude 712c may also cause the follower 606 to locate and ultimately be received within the pocket 708.

Advantageously, the capstan assembly 602 may define or otherwise provide one or more cutouts 714 along the actuation pathway 710. The cutout(s) 714 may comprise a void or open area defined in the capstan assembly 602 that extends to the first (or "bottom-most") structural level 702a. The cutout(s) 714 may be configured to ensure that the capstan assembly 602 is rotated precisely in accordance with the predetermined rotational sequence, otherwise the follower 606 (FIGS. 7A and 7C) will encounter the cutout(s) 714. Upon encountering the cutout(s) 714, the follower 606 will fall into the cutout(s) 714 and return to the first structural level 702a under the spring force released by the coil spring 608 (FIG. 7A). Upon reaching the first structural level 702a, the follower 606 must traverse the actuation pathway 710 from the beginning and otherwise start over.

Importantly, each ramp 706a-c is keyed and otherwise located at corresponding predetermined angular locations. Consequently, the capstan assembly 602 must be precisely rotated in accordance with the predetermined rotational sequence or else the follower 606 (FIGS. 7A and 7C) will not locate or be able to ride up the ramps 706a-c. Instead, the follower 606 may risk encountering the cutout(s) 714, which returns the follower 606 to the first structural level 702a and requires the follower 706 to traverse the actuation pathway 710 from the beginning. Moreover, each ramp 706a-c may comprise a living hinge that allows the follower 606 to traverse under the ramp 706a-c when the capstan assembly 602 is rotated in one angular direction, but allows the follower 606 to engage and ride up the ramp 706a-c when the capstan assembly 602 is rotated in the opposite angular direction. Consequently, the capstan assembly 602 must again be precisely rotated in accordance with the predetermined rotational sequence or else the follower 606 will not probably engage or ride up the ramps 706a-c.

FIG. 7C is another enlarged, isometric view of the indicator assembly 220 of FIG. 7A, according to one or more embodiments. As illustrated, the follower 606 has successfully traversed the actuation pathway 710 (FIG. 7B) and is shown received within the pocket 708. Once the follower 606 is received within the pocket 708, the top or upper end 716 of the indicator shaft 222 will protrude (extend) a short distance out of the drive housing 208 (FIGS. 5A-5B) to provide a positive, visual indication that the surgical tool 200 (FIG. 2) has exhausted its useful life. Moreover, since the follower 606 and the indicator mount 604 are stationary and grounded to the drive housing 208 (FIG. 6), once the follower 606 is received within the pocket 708, the follower 606 will bind against the sidewalls of the pocket 708 and thereby prevent the capstan assembly 602 from further rotation in either angular direction. As a result, the indicator assembly 220 will be prevented from returning to the non-activated state without entirely disassembling the drive housing 208.

The ramps 706a-c, the cutout(s) 714, and the predetermined rotational sequence required to successfully traverse the actuation pathway 710 (FIG. 7B) may each be considered fail-safes that ensure that the indicator assembly 220 is not inadvertently or prematurely transitioned to the activated state. For example, following each surgical operation, the surgical tool 200 (FIG. 2) must be removed from the robotic manipulator and cleaned, sterilized, and processed before being placed back into active duty. During the cleaning and sterilizing process, an operator (technician) may inadvertently rotate the first drive input 406a. Because the first drive input 406a must be rotated in the precise combination of clockwise and counter-clockwise rotations in accordance with the predetermined rotational sequence, it is virtually impossible for an operator to inadvertently trigger actuation of the indicator assembly 220 to the activated state.

FIG. 8A is an enlarged, isometric view of another example indicator assembly 800, according to one or more additional embodiments. The indicator assembly 800 may be similar in some respects to the indicator assembly 220 of FIGS. 6 and 7A-7C, and therefore may be best understood with reference thereto. In at least one embodiment, the indicator assembly 800 may replace the indicator assembly 220 within the drive housing 208 (FIG. 6), and therefore may be used in conjunction with the surgical tool 200 (FIG. 2).

In the illustrated embodiment, the indicator assembly 800 includes a capstan assembly 802 operatively coupled to or extending from the first drive input 406a such that actuation of the first drive input 406a results in rotation of the capstan assembly 802. The indicator assembly 800 further includes an indicator mount 804, which may be rotatably mounted to the drive housing 208 (FIG. 6) and rotatable about a longitudinal axis $D_1$.

As illustrated, a spring-loaded arm 806 extends from or otherwise forms part of the indicator mount 804, and a follower 808 extends from an end of the arm 806 such that the follower 808 moves simultaneously with the arm 806 as the indicator mount 804 rotates about the longitudinal axis $D_1$. In the illustrated embodiment, the follower 808 may comprise a rod or pin that extends orthogonally from the arm 806. As described in more detail below, the follower 808 may be configured to be received within a channel defined by the capstan assembly 802.

The indicator assembly 800 further includes an indicator shaft 810, similar in some respects to the indicator shaft 222 of FIGS. 6 and 7A-7C, and therefore may be best understood with reference thereto. The indicator shaft 810 may form part of or otherwise extend from the indicator mount 804 such that as the indicator mount 804 rotates about the longitudinal axis $D_1$, the indicator shaft 810 correspondingly rotates in the same angular direction. The longitudinal axis $D_1$ may be coaxially aligned with the indicator aperture 502 (FIGS. 5A-5B) defined in the drive housing 208 (FIG. 6).

The indicator assembly 800 may further include a shaft 812 extending from or otherwise forming an integral part of the indicator mount 804. The shaft may be rotatably mounted to the drive housing 208 (FIG. 6), or another static structure secured to the drive housing 208. In some embodiments, as illustrated, the shaft 812 may be received within a receptacle 814 either forming part of the drive housing 208 or otherwise rigidly secured to the drive housing 208. A torsion spring 816 may be operatively coupled to the indicator mount 804 and configured to naturally and continuously bias the indicator mount 804 and the interconnected follower 808 toward the central axis $C_1$ of the capstan assembly 802. In the illustrated embodiment, the torsion spring 816 extends about the shaft 812, but could alternatively be mounted in yet other locations related to the indicator mount 804.

The indicator assembly 800 may further include a coil spring 818 that extends about a portion of the indicator shaft 810 and urges the indicator shaft 810 to move vertically upward along the longitudinal axis $D_1$ in the direction E. The bottom of the coil spring 818 may engage or be mounted to a portion of the indicator mount 804, such as a receptacle 820 secured to or forming part of the indicator mount 804. The top of the coil spring 818 may engage a portion the indicator shaft 810 such that when the indicator shaft 810 is released, as described below, the spring force of the coil spring 818 will cause the indicator shaft 810 to move upwards in the direction E and along the longitudinal axis $D_1$.

The indicator shaft 810 may be releasably coupled to a vertically static structure; i.e., a structure that is unable to move vertically and otherwise along the longitudinal axis $D_1$. In some embodiments, the vertically static structure may comprise the receptacle 820, but could alternatively include other vertically static structures provided within or forming part of the drive housing 208 (FIG. 6). In the illustrated embodiment, the indicator shaft 810 provides and otherwise defines a lateral projection 822 extending laterally from the main body of the indicator shaft 810. In some embodiments, the lateral projection 822 may be releasably coupled to the vertically static structure (e.g., the receptacle 820) via a bayonet connection, a pin and slot configuration, or the like. In such embodiments, as the indicator mount 804 rotates about the longitudinal axis $D_1$, as described herein, the lateral projection 822 may be released from the vertically static structure. Once the lateral projection 822 is released from the vertically static structure, the spring force of the coil spring 818 may be released to advance the indicator shaft 810 vertically in the direction E and along the longitudinal axis $D_1$. As indicated above, the longitudinal axis $D_1$ may be coaxially aligned with the indicator aperture 502 (FIGS. 5A-5B) of the drive housing 208 (FIG. 6), thus advancing the indicator shaft 810 in the direction E effectively transitions the indicator assembly 800 to the activated state.

The capstan assembly 802 either forms part of or extends from the first drive input 406a, and is rotatable about the central axis $C_1$ as the first drive input 406a is rotated. As illustrated, the capstan assembly 802 may include a plurality of disc keys, shown as a first disc key 824a, a second disc key 824b, and a third disc key 824c. The disc keys 824a-c are arranged concentric and coaxially aligned with the central axis $C_1$ and slidably engageable with vertically adjacent disc keys 824a-c. Each disc key 824a-c provides and otherwise defines one or more radial shoulders 826 and a slot 828. To actuate the indicator assembly 800 and thereby transition the indicator assembly 800 to the activated state, the slots 828 in each disc key 824a-c must align axially, thereby allowing the follower 808 to enter a channel 830 (see FIG. 8B) that forms and is otherwise created when the slots 828 axially align.

Axially aligning the slots 828 can be accomplished by rotating the capstan assembly 802 in a predetermined rotational sequence comprising a precise combination of clockwise and counter-clockwise rotations. The combination of precise rotational movements required to transition the indicator assembly 800 to the activated state may be sufficiently complex such that inadvertent matching of the predetermined rotational sequence will occur in extremely rare circumstances.

Rotation of the capstan assembly 802 will be dictated by actuation of the first drive input 406a. Once the predetermined operational threshold of the surgical tool 200 (FIG. 2) has been reached and acknowledged, the robotic manipulator of the tool driver may be programmed to actuate the first drive input 406a in the predetermined rotational sequence, and thereby transition the indicator assembly 800 to the activated state.

In the illustrated embodiment, the predetermined rotational sequence may include rotating the first drive input 406a in a first angular direction (e.g., counter-clockwise) for a first predetermined angular magnitude. As indicated above, the first disc key 824a may be secured to the first drive input 406a, thus rotating the first drive input 406a in the first angular direction correspondingly rotates the first disc key 824a in the same angular direction. The first disc key 824a may be rotated in the first angular direction for the first predetermined angular magnitude until opposing radial shoulders 826 defined on the first and second disc keys 824a,b engage. In some embodiments, at this point the slots 828 of the first and second disc keys 824a,b are aligned axially.

The predetermined rotational sequence may then include changing angular direction by rotating the first drive input 406a, and therefore the first and second disc keys 824a,b, in a second angular direction (e.g., clockwise) for a second predetermined angular magnitude. The first and second disc keys 824a,b may be rotated in the second angular direction for the second predetermined angular magnitude until opposing radial shoulders 826 defined on the second and third disc keys 824b,c engage. Once the opposing radial shoulders 826 defined on the first and second disc keys 824a,b engage, further rotation of the first disc key 824a, and therefore the second disc key 824b, will drive the radial shoulders 826 of the second disc 824b to engage with the radial shoulders 826 of the third disc 824c. As the direction of rotation changes, friction will keep the third disc key 824c in place, while the opposing face of the radial shoulder 826 of the first disc 824a can drive the second disc key 824b to an axially aligned position with the third disc key 824b. In some embodiments, at this point the slots 828 of the first, second, and third disc keys 824a-c become aligned axially, thus forming the channel 830 (FIG. 8B).

The predetermined rotational sequence may then include changing angular direction again and rotating first drive input 406a, and therefore the first, second, and third disc keys 824a-c, in the first angular direction (e.g., counter-clockwise) for a third predetermined angular magnitude. Rotating the first, second, and third disc keys 824a-c in the first angular direction for the third angular magnitude may be configured to align the channel 830 (FIG. 8B) with the follower 808 and thereby allow the follower 808 to enter the channel 830.

FIG. 8B is another enlarged, isometric view of the indicator assembly 800 of FIG. 8A, according to one or more additional embodiments. In FIG. 8B, the indicator assembly 800 has been actuated and otherwise transitioned to the activated state. More specifically, as the slots 828 defined in the first, second, and third disc keys 824a-c align axially, as described above, the channel 830 is created and otherwise defined by the capstan assembly 802. Once the capstan assembly 802 is rotated to angularly align the channel 830 with the follower 808, as described above, the spring force of the torsion spring 816 will naturally urge the indicator mount 804 to rotate about the longitudinal axis $D_1$ in the direction F. Rotating the indicator mount 804 in the direction F will correspondingly move the arm 806 and the follower 808 in the same direction and thereby inserting (receiving) the follower 808 within the channel 830.

Rotating the indicator mount 804 about the longitudinal axis $D_1$ in the direction F will correspondingly and simultaneously rotate the indicator shaft 810 in the same angular direction. As the indicator shaft 810 rotates in the direction F, the indicator shaft 810 will be released from the vertically static structure (e.g., the receptacle 820). More specifically, in applications where the vertically static structure comprises the receptacle 820, and the indicator shaft 810 is removably coupled to the receptacle 820, rotating the indicator shaft 810 about the longitudinal axis $D_1$ will correspondingly release the lateral projection 822 from the receptacle 820. Once the lateral projection 822 is released from the vertically static structure, the spring force of the coil spring 818 may be released to advance the indicator shaft 810 vertically in the direction E and along the longitudinal axis $D_1$, thereby transitioning the indicator assembly 800 to the activated state.

Notably, once the follower 808 is received within the channel 830, the capstan assembly 802 will be prevented from further rotation in either angular direction. As a result, the indicator assembly 800 will be prevented from returning to the non-activated state without entirely disassembling the drive housing 208 and resetting the indicator assembly 800.

In some embodiments, instead of the indicator shaft 810 extending vertically in the direction E to transition the indicator assembly 800 to the activated state, it is contemplated herein that actuation of the indicator assembly 800 may drive a variety of other features configured to communicate to the user that the instrument has reached its end of life. In other embodiments, for example, the indicator shaft 810 could be replaced with a visual opening in the drive housing 208 (FIG. 6) showing a state change triggered by actuation of the indicator mount 804. Alternatively, a portion of the drive housing 208 could be displaced to indicate end of life of the surgical tool 200 (FIG. 2).

Figure 9:
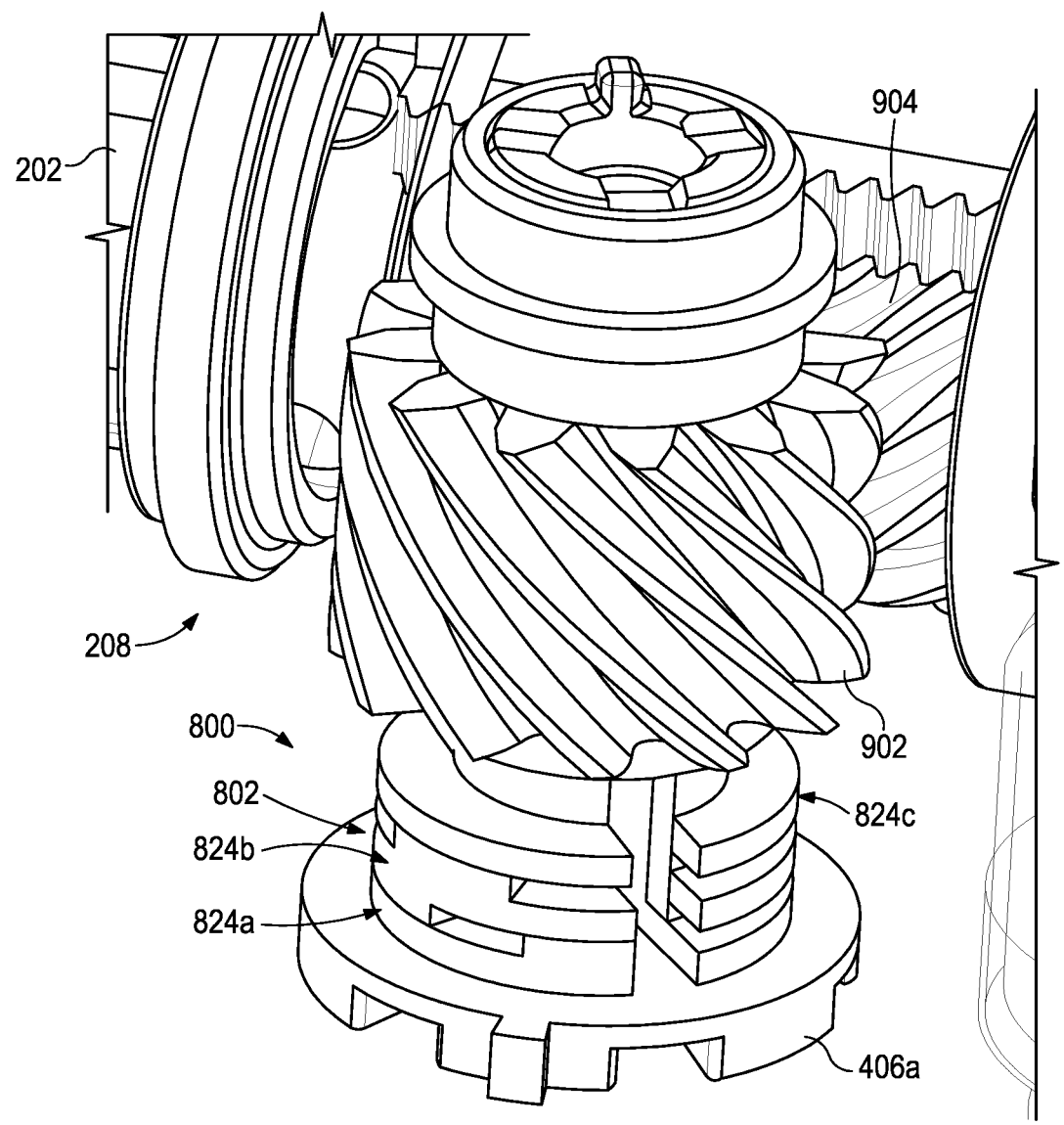
FIG. 9 is an enlarged, isometric view of the indicator assembly of FIGS. 8A-8B, in conjunction with a secondary function, according to one or more embodiments.

FIG. 9 is an enlarged, isometric view of the indicator assembly 800 of FIGS. 8A-8B, in conjunction with a secondary function, according to one or more embodiments. More specifically, FIG. 9 shows an example embodiment where the indicator assembly 800 may be used not only to indicate the termination of the useful life of the surgical tool 200 (FIG. 2), but may also form part of a secondary operational function of the surgical tool 200.

In the illustrated embodiment, the capstan assembly 802 includes the first drive input 406a and the disc keys 824a-c, as generally described above. However, the capstan assembly 802 further includes a drive gear 902, shown as a worm gear, arranged within the drive housing 208 to engage and drive a corresponding driven gear 904. As the capstan assembly 802 is actuated, via operation of the first drive input 406a, the drive gear 902 may drive the driven gear 904 to undertake one or more functions of the surgical tool 200 (FIG. 2). In one embodiment, for example, driving the driven gear 904 may cause the shaft 202 to rotate about its longitudinal axis $A_1$ (FIG. 2). In other embodiments, however, driving the driven gear 904 may carry out other functions or operations, without departing from the scope of the disclosure.

Accordingly, the indicator assembly 800 may be used in conjunction with an 'active' capstan or series of active capstans. In such embodiments, actuation of the indicator assembly 800 to the "activated" state would still require a precise combination of clockwise and counter-clockwise rotations, which would cause unique operation of the surgical tool (FIG. 2) via interaction between the drive and driven gears 902, 904. In at least one embodiment, the robotic system could monitor movements in a clinical setting to guarantee that the indicator assembly 800 would not be activated prematurely and intraoperatively. In any event, because of the precise combination of clockwise and counter-clockwise rotations required to actuate the indicator assembly 800, the chances of the first drive input 406a being inadvertently and prematurely rotated in the precise combination would be sufficiently complex and would only be triggered inadvertently on rare circumstances.

FIGS. 10A-10B are enlarged, isometric assembled and exploded views, respectively, of another example indicator assembly 1000, according to one or more additional embodiments. The indicator assembly 1000 may be similar in some respects to the indicator assemblies 220 and 800 of FIGS. 6, 7A-7C, and 8A-8B, and therefore may be best understood with reference thereto. In at least one embodiment, the indicator assembly 1000 may replace the indicator assembly 220 within the drive housing 208 (FIG. 6), and may thus be used in conjunction with the surgical tool 200 (FIG. 2).

As illustrated, the indicator assembly 1000 includes a capstan assembly 1002 that extends from and otherwise forms part of the first drive input 406a. The capstan assembly 1002 may include a central shaft 1004 having a first or "lower" end 1006a and a second or "upper" end 1006b opposite the lower end 1006a. The lower end 1006a may be operatively coupled to or form an integral extension of the first drive input 406a, and may extend along the central axis $C_1$.

A torsion spring 1008 extends about the central shaft 1004 and has a first or "lower" end 1010a and a second or "upper" end 1010b. The lower end 1010a may be operatively coupled to the first drive input 406a. In the illustrated embodiment, for example, the lower end 1010a may be received within a pocket or slot 1012 defined in the first drive input 406a. In contrast, when the indicator assembly 1000 is installed in the drive housing 208 (FIG. 6), the upper end 1010b may be secured to a static portion of the drive housing 208 or another static feature housed within the drive housing 208. As a result, as the first drive input 406a rotates, the torsion spring 1008 is configured to resist rotation of the capstan assembly 1002.

The capstan assembly 1002 may further include a receptacle 1014 arranged or otherwise provided at the upper end 1006b of the central shaft 1004. As best seen in FIG. 10B, the receptacle 1014 provides or defines a central aperture 1016. The receptacle 1014 also provides or defines a release notch 1018 that forms a part of the central aperture 1016.

The capstan assembly 1002 may also include an indicator mount 1020 sized to be received at least partially within the central aperture 1016. More specifically, the indicator mount 1020 includes a lower extension 1022 (FIG. 10B) extendable into the central aperture 1016. The indicator mount 1020 may also provide a lateral projection 1024. When the indicator assembly 1000 is installed in the drive housing 208 (FIG. 6), the lateral projection 1024 may be coupled to a rotationally static portion of the drive housing 208 or another rotationally static feature provided within the drive housing 208. The term "rotationally static portion" refers to a portion of the drive housing 208 or other feature within the drive housing 208 that will prevent the indicator mount 1020 from rotating about the central axis $C_1$, but will allow the indicator mount 1020 to move vertically along the central axis $C_1$ when the indicator assembly 1000 is actuated to the activated state.

As illustrated, a follower or "release member" 1026 (FIG. 10B) may be provided and otherwise defined on the outer radial surface of the lower extension 1022. In some embodiments, the release member 1026 may comprise a radial projection or protrusion extending radially outward from the outer radial surface of the lower extension 1022. The release member 1026 may be sized to be received by and through the release notch 1018 when the capstan assembly 1002, and more particularly the central shaft 1004 and the receptacle 1014, is rotated about the central axis $C_1$ to align the release notch 1018 with the release member 1026.

The capstan assembly 1002 further includes an indicator shaft 1028 that extends from and otherwise forms an integral part or extension of the indicator mount 1020. The indicator shaft 1028 extends along the central axis $C_1$, which is coaxially aligned with the indicator aperture 502 (FIGS. 5A-5B) of the drive housing 208 (FIG. 6). Consequently, moving the indicator shaft 1028 upwards along the central axis $C_1$ will extend the indicator shaft 1028 through the indicator aperture 502 and effectively transition the indicator assembly 1000 to the activated state.

The indicator assembly 1000 may further include a mounting shaft 1030 (FIG. 10B) extending from or otherwise forming an integral part of the indicator mount 1020. In the illustrated embodiment, the mounting shaft 1030 extends from the lower extension 1022, and extends coaxially with the central axis $C_1$. The mounting shaft 1030 may be sized and otherwise configured to be received within the central aperture 1016. A coil spring 1032 (FIG. 10B) may extend about a portion of the mounting shaft 1030 to naturally urge the indicator mount 1020, including the indicator shaft 1028, to move vertically upward along the longitudinal axis $C_1$. The bottom of the coil spring 1032 may engage or be mounted to the central shaft 1004 at a bottom (not visible) of the central aperture 1016. The top of the coil spring 1032 may engage a portion the indicator mount 1020, such as the bottom of the lower extension 1022. When the indicator mount 1020 is properly mounted to the central shaft 1004 and the indicator assembly 1000 is assembled within the drive housing (FIG. 6), the coil spring 1032 may be compressed within the central aperture 1016. When the indicator shaft 1028 is released, as described below, the spring force of the coil spring 1032 will cause the indicator shaft 1028 to move upwards and along the longitudinal axis $C_1$.

Actuation of the indicator assembly 1000 from the non-activated state, where the indicator shaft 1028 is not visible to the user (operator), to the activated state, where the indicator shaft 1028 is visible to the user, will be dictated by actuation of the first drive input 406*a*. Once the predetermined operational threshold of the surgical tool 200 (FIG. 2) has been reached and acknowledged, the robotic manipulator of the tool driver may be programmed to actuate the first drive input 406*a* and thereby transition the indicator assembly 1000 to the activated state.

More specifically, the first drive input 406*a* may be rotated, which will correspondingly rotate the central shaft 1004 in the same angular direction. The coil spring 1006 will resist rotation of the first drive input 406*a*, but the spring force of the coil spring 1006 can be overcome with sufficient torque provided by the first drive input 406*a*. As the central shaft 1004 rotates, the indicator mount 1020 remains stationary relative to the receptacle 1014 since the lateral projection 1024 is rotationally secured to a rotationally static portion of the drive housing 208, as generally described above.

Continuing to overcome the spring force of the coil spring 1006 and thereby rotating the central shaft 1004 will eventually align the release notch 1018 with the release member 1026. Once the release notch 1018 aligns with the release member 1026, the release member 1026 may be able to received within and extend through the release notch, which allows the spring force of the coil spring 1032 to be released. Releasing the spring force of the coil spring 1032 causes the indicator mount 1020 and, more particularly, the indicator shaft 1028, to move vertically along the central axis $C_1$, thus enabling the indicator shaft 1028 to extend through the indicator aperture 502 (FIGS. 5A-5B) of the drive housing 208 (FIGS. 5A-5B and 6). Extending the indicator shaft 1028 through the indicator aperture 502 effectively transitions the indicator assembly 1000 to the activated state.

Notably, the spring force of the coil spring 1006 may be rated high enough such that a user (technician) that is cleaning or sterilizing the surgical tool 200 (FIG. 2) will be practically unable to manually overcome the spring force. Consequently, manually and inadvertently actuating the indicator assembly 1000 prematurely will occur in only extremely rare circumstances.

Embodiments disclosed herein include:

A. A surgical tool that includes a drive housing defining an indicator aperture, a drive input rotatably coupled to a bottom of the drive housing, and an indicator assembly arranged within the drive housing and actuatable to provide visual indication that the surgical tool has exhausted its useful life, the indicator assembly including a capstan assembly operatively coupled to the drive input such that rotation of the drive input correspondingly rotates the capstan assembly, an indicator mount secured to the drive housing, and an indicator shaft extending from the indicator mount along a longitudinal axis coaxially aligned with the indicator aperture, wherein the capstan assembly is rotated with the drive input to actuate the indicator assembly between a non-activated state, where the indicator shaft is recessed into the indicator aperture, and an activated state, where the indicator shaft extends out of the drive housing via the indicator aperture to provide the visual indication.

B. A method of operating a surgical tool that includes determining that a useful life of the surgical tool has been exhausted, the surgical tool including a drive housing defining an indicator aperture, a drive input rotatably coupled to a bottom of the drive housing, and an indicator assembly arranged within the drive housing, the indicator assembly including a capstan assembly operatively coupled to the drive input such that rotation of the drive input correspondingly rotates the capstan assembly, an indicator mount secured to the drive housing, and an indicator shaft extending from the indicator mount along a longitudinal axis coaxially aligned with the indicator aperture. The method further including rotating the drive input and thereby rotating the capstan assembly and actuating the indicator assembly between a non-activated state, where the indicator shaft is recessed into the indicator aperture, and an activated state, where the indicator shaft extends out of the drive housing via the indicator aperture, and providing a visual indication with the indicator shaft that the useful life of the surgical tool has been exhausted.

Each of embodiments A and B may have one or more of the following additional elements in any combination: Element 1: wherein the indicator assembly is actuated to the activated state by rotating the capstan assembly with the drive input in a predetermined rotational sequence comprising a combination of clockwise and counter-clockwise rotations. Element 2: wherein the indicator mount is secured to the drive housing such that the indicator mount and the indicator shaft are constrained within the drive housing to movement along the longitudinal axis, the indicator assembly further including a follower extending from the indicator mount and engageable with the capstan assembly. Element 3: wherein the capstan assembly includes a plurality of structural levels axially offset from each other along a central axis of the capstan assembly, each structural level including a planar surface parallel to the planar surface of vertically adjacent structural levels, and one or more ramps providing a vertical transition between the vertically adjacent structural levels, wherein, as the capstan assembly is rotated in the predetermined rotational sequence, the follower progressively and sequentially engages each structural level by engaging and riding up each ramp, and wherein, as the follower transitions to each structural level, the indicator mount and the indicator shaft correspondingly move vertically along the longitudinal axis and toward the indicator aperture. Element 4: wherein the capstan assembly further includes a pocket defined in a top-most structural level of the plurality of structural levels, and wherein the follower is received within the pocket upon completing the predetermined rotational sequence. Element 5: wherein the indicator assembly further includes a cutout defined in the capstan assembly and extending to a bottom-most structural level of the plurality of structural levels, and a coil spring extending about the indicator shaft and operable to build spring force as the follower progressively and sequentially engages each structural level, wherein, when the capstan assembly is not rotated in the predetermined rotational sequence, the follower falls into the cutout and the coil spring releases the spring force to urge the follower to the bottom-most structural level. Element 6: wherein a bottom of the coil spring engages the indicator mount, and a top of the coil spring engages a static portion of the drive housing. Element 7: wherein at least one of the one or more ramps comprises a living hinge allowing the follower to traverse under the at least one of the one or more ramps when the capstan assembly is rotated in a first angular direction, and allowing the follower to engage and ride up the at least one of the one or more ramps when the capstan assembly is rotated in a second angular direction opposite the first angular direction. Element 8: wherein the indicator mount is rotatably mounted to the drive housing and rotatable about the longitudinal axis, the indicator assembly further including an arm extending from the indicator mount, and a follower extending from an end of the arm, wherein the arm is spring-loaded and urges the follower into engagement with the capstan assembly. Element 9: wherein the capstan assembly includes a plurality of disc keys coaxially aligned with a central axis of the capstan assembly, each disc key defining a slot, wherein, as the capstan assembly is rotated in the predetermined rotational sequence, the slot in each disc key aligns with vertically adjacent slots to form a channel in the capstan assembly, and wherein the follower is biased into the channel with the arm as the indicator mount rotates about the longitudinal axis. Element 10: wherein the indicator shaft is releasably coupled to the indicator mount as the indicator mount rotates about the longitudinal axis, and wherein a coil spring is arranged to urge the indicator shaft vertically along the longitudinal axis when the indicator shaft is released from the indicator mount. Element 11: wherein the capstan assembly further includes a central shaft having opposing lower and upper ends, the lower end extending from the drive input, a torsion spring extending about the central shaft and having a first end operatively coupled to the drive input and a second end secured to the drive housing such that rotation of the central shaft is resisted by the torsion spring, and a receptacle provided at the upper end and defining a central aperture sized to releasably receive a portion of the indicator mount, wherein the indicator assembly is actuated to the activated state by rotating the central shaft with the drive input to overcome spring force of the torsion spring, and thereby release the indicator mount and the indicator shaft from the receptacle. Element 12: wherein the indicator mount provides a lateral projection secured to a rotationally static portion of the drive housing. Element 13: wherein the receptacle defines a release notch and the indicator mount provides a release member alignable with the release notch as the central shaft is rotated to overcome the spring force, and wherein the capstan assembly further includes a coil spring that releases and causes the indicator mount and the indicator shaft to move vertically along the longitudinal axis when the release notch aligns with the release member.

Element 14: wherein rotating the drive input and thereby actuating the indicator assembly between the non-activated state and the activated state comprises rotating the capstan assembly with the drive input in a predetermined rotational sequence comprising a combination of clockwise and counter-clockwise rotations. Element 15: wherein the indicator assembly further includes a follower extending from the indicator mount and engageable with the capstan assembly, and the capstan assembly includes a plurality of structural levels axially offset from each other and each structural level including a planar surface parallel to the planar surface of vertically adjacent structural levels, the method further comprising rotating the capstan assembly in the predetermined rotational sequence with the drive input, progressively and sequentially engaging each structural level with the follower as the capstan assembly is rotated in the predetermined rotational sequence, and moving the indicator mount and the indicator shaft vertically along the longitudinal axis and toward the indicator aperture as the follower transitions to each structural level. Element 16: wherein the capstan assembly further includes one or more ramps providing a vertical transition between the vertically adjacent structural levels, the method further comprising engaging the follower on the one or more ramps and thereby transitioning the follower between vertically adjacent structural levels of the plurality of structural levels, and moving the indicator mount and the indicator shaft vertically along the longitudinal axis and toward the indicator aperture as the follower engages the one or more ramps. Element 17: wherein the indicator assembly further includes a cutout defined in the capstan assembly and extending to a bottom-most structural level of the plurality of structural levels, and a coil spring extending about the indicator shaft, the method further comprising rotating the capstan assembly in a manner different from the predetermined rotational sequence, encountering the cutout with the follower as the capstan assembly is rotated in the manner different from the predetermined rotational sequence, and returning the follower to the bottom-most structural level as the follower falls into the cutout. Element 18: wherein at least one of the one or more ramps comprises a living hinge, the method further comprising allowing the follower to traverse under the at least one of the one or more ramps when the capstan assembly is rotated in a first angular direction, and allowing the follower to engage and ride up the at least one of the one or more ramps when the capstan assembly is rotated in a second angular direction opposite the first angular direction. Element 19: wherein the indicator assembly further includes an arm extending from the indicator mount, and a follower extending from an end of the arm, and wherein the capstan assembly includes a plurality of disc keys and coaxially aligned with a central axis of the capstan assembly, each disc key defining a slot, the method further comprising rotating the capstan assembly in the predetermined rotational sequence with the drive input, aligning the slot of each disc key with vertically adjacent slots and thereby forming a channel in the capstan assembly, and biasing the follower into the channel with the arm once the channel is formed. Element 20: wherein the indicator shaft is releasably coupled to the indicator mount as the indicator mount rotates about the longitudinal axis, the method further comprising urging the indicator shaft vertically along the longitudinal axis with a coil spring when the indicator shaft is released from the indicator mount. Element 21: wherein the capstan assembly further includes a central shaft extending from the drive input, a torsion spring extending about the central shaft, and a receptacle provided at the upper end and defining a central aperture sized to releasably receive a portion of the indicator mount, the method further comprising resisting rotation of the central shaft with the torsion spring, and operating the drive input to overcome a spring force of the torsion spring and thereby releasing the indicator mount and the indicator shaft from the receptacle. Element 22: wherein the receptacle defines a release notch and the indicator mount provides a release member alignable with the release notch, the method further comprising rotating the central shaft and thereby aligning the release notch with the release member, releasing the indicator mount and the indicator shaft from the receptacle once the release notch aligns with the release member, and moving the indicator mount and the indicator shaft vertically along the longitudinal axis with a coil spring when the release notch aligns with the release member. Element 23: wherein the capstan assembly further includes a drive gear arranged to drive a driven gear positioned within the drive housing, and wherein determining that the useful life of the surgical tool has been exhausted is preceded by rotating the drive input and thereby driving the driven gear with the drive gear, and performing a secondary function of the surgical tool as the driven gear is rotated with the drive gear.

By way of non-limiting example, exemplary combinations applicable to A and B include: Element 1 with Element 2; Element 2 with Element 3; Element 3 with Element 4; Element 3 with Element 5; Element 5 with Element 6; Element 3 with Element 7; Element 1 with Element 8; Element 8 with Element 9; Element 9 with Element 10; Element 11 with Element 12; Element 11 with Element 13; Element 14 with Element 15; Element 15 with Element 16;

Element 17 with Element 18; Element 17 with Element 19; Element 15 with Element 19; Element 19 with Element 20; and Element 21 with Element 22.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
 a drive housing defining an indicator aperture;
 a drive input rotatably coupled to a bottom of the drive housing; and
 an indicator assembly arranged within the drive housing and actuatable to provide visual indication that the surgical tool has exhausted its useful life, the indicator assembly including:
  a capstan assembly operatively coupled to the drive input such that rotation of the drive input correspondingly rotates the capstan assembly;
  an indicator mount secured to the drive housing; and
  an indicator shaft extending from the indicator mount along a longitudinal axis coaxially aligned with the indicator aperture,
 wherein the capstan assembly is rotated with the drive input to actuate the indicator assembly between a non-activated state, where the indicator shaft is recessed into the indicator aperture, and an activated state, where the indicator shaft extends out of the drive housing via the indicator aperture to provide the visual indication.

2. The surgical tool of claim 1, wherein the indicator assembly is actuated to the activated state by rotating the capstan assembly with the drive input in a predetermined rotational sequence comprising a combination of clockwise and counter-clockwise rotations.

3. The surgical tool of claim 2, wherein the indicator mount is secured to the drive housing such that the indicator mount and the indicator shaft are constrained within the drive housing to movement along the longitudinal axis, the indicator assembly further including a follower extending from the indicator mount and engageable with the capstan assembly.

4. The surgical tool of claim 3, wherein the capstan assembly includes:
 a plurality of structural levels axially offset from each other along a central axis of the capstan assembly, each structural level including a planar surface parallel to the planar surface of vertically adjacent structural levels; and
 one or more ramps providing a vertical transition between the vertically adjacent structural levels,
 wherein, as the capstan assembly is rotated in the predetermined rotational sequence, the follower progressively and sequentially engages each structural level by engaging and riding up each ramp, and
 wherein, as the follower transitions to each structural level, the indicator mount and the indicator shaft correspondingly move vertically along the longitudinal axis and toward the indicator aperture.

5. The surgical tool of claim 4, wherein the capstan assembly further includes a pocket defined in a top-most structural level of the plurality of structural levels, and wherein the follower is received within the pocket upon completing the predetermined rotational sequence.

6. The surgical tool of claim 4, wherein the indicator assembly further includes:
 a cutout defined in the capstan assembly and extending to a bottom-most structural level of the plurality of structural levels; and
 a coil spring extending about the indicator shaft and operable to build spring force as the follower progressively and sequentially engages each structural level,
 wherein, when the capstan assembly is not rotated in the predetermined rotational sequence, the follower falls into the cutout and the coil spring releases the spring force to urge the follower to the bottom-most structural level.

7. The surgical tool of claim 6, wherein a bottom of the coil spring engages the indicator mount, and a top of the coil spring engages a static portion of the drive housing.

8. The surgical tool of claim 4, wherein at least one of the one or more ramps comprises a living hinge allowing the follower to traverse under the at least one of the one or more ramps when the capstan assembly is rotated in a first angular direction, and allowing the follower to engage and ride up the at least one of the one or more ramps when the capstan assembly is rotated in a second angular direction opposite the first angular direction.

9. The surgical tool of claim 2, wherein the indicator mount is rotatably mounted to the drive housing and rotatable about the longitudinal axis, the indicator assembly further including:
   an arm extending from the indicator mount; and
   a follower extending from an end of the arm, wherein the arm is spring-loaded and urges the follower into engagement with the capstan assembly.

10. The surgical tool of claim 9, wherein the capstan assembly includes a plurality of disc keys coaxially aligned with a central axis of the capstan assembly, each disc key defining a slot,
   wherein, as the capstan assembly is rotated in the predetermined rotational sequence, the slot in each disc key aligns with vertically adjacent slots to form a channel in the capstan assembly, and
   wherein the follower is biased into the channel with the arm as the indicator mount rotates about the longitudinal axis.

11. The surgical tool of claim 10, wherein the indicator shaft is releasably coupled to the indicator mount as the indicator mount rotates about the longitudinal axis, and wherein a coil spring is arranged to urge the indicator shaft vertically along the longitudinal axis when the indicator shaft is released from the indicator mount.

12. The surgical tool of claim 1, wherein the capstan assembly further includes:
   a central shaft having opposing lower and upper ends, the lower end extending from the drive input;
   a torsion spring extending about the central shaft and having a first end operatively coupled to the drive input and a second end secured to the drive housing such that rotation of the central shaft is resisted by the torsion spring; and
   a receptacle provided at the upper end and defining a central aperture sized to releasably receive a portion of the indicator mount,
   wherein the indicator assembly is actuated to the activated state by rotating the central shaft with the drive input to overcome spring force of the torsion spring, and thereby release the indicator mount and the indicator shaft from the receptacle.

13. The surgical tool of claim 12, wherein the indicator mount provides a lateral projection secured to a rotationally static portion of the drive housing.

14. The surgical tool of claim 12, wherein the receptacle defines a release notch and the indicator mount provides a release member alignable with the release notch as the central shaft is rotated to overcome the spring force, and
   wherein the capstan assembly further includes a coil spring that releases and causes the indicator mount and the indicator shaft to move vertically along the longitudinal axis when the release notch aligns with the release member.

15. A method of operating a surgical tool, comprising:
   determining that a useful life of the surgical tool has been exhausted, the surgical tool including a drive housing defining an indicator aperture, a drive input rotatably coupled to a bottom of the drive housing, and an indicator assembly arranged within the drive housing, the indicator assembly including:
      a capstan assembly operatively coupled to the drive input such that rotation of the drive input correspondingly rotates the capstan assembly;
      an indicator mount secured to the drive housing; and
      an indicator shaft extending from the indicator mount along a longitudinal axis coaxially aligned with the indicator aperture;
   rotating the drive input and thereby rotating the capstan assembly and actuating the indicator assembly between a non-activated state, where the indicator shaft is recessed into the indicator aperture, and an activated state, where the indicator shaft extends out of the drive housing via the indicator aperture; and
   providing a visual indication with the indicator shaft that the useful life of the surgical tool has been exhausted.

16. The method of claim 15, wherein rotating the drive input and thereby actuating the indicator assembly between the non-activated state and the activated state comprises rotating the capstan assembly with the drive input in a predetermined rotational sequence comprising a combination of clockwise and counter-clockwise rotations.

17. The method of claim 16, wherein the indicator assembly further includes a follower extending from the indicator mount and engageable with the capstan assembly, and the capstan assembly includes a plurality of structural levels axially offset from each other and each structural level including a planar surface parallel to the planar surface of vertically adjacent structural levels, the method further comprising:
   rotating the capstan assembly in the predetermined rotational sequence with the drive input;
   progressively and sequentially engaging each structural level with the follower as the capstan assembly is rotated in the predetermined rotational sequence; and
   moving the indicator mount and the indicator shaft vertically along the longitudinal axis and toward the indicator aperture as the follower transitions to each structural level.

18. The method of claim 17, wherein the capstan assembly further includes one or more ramps providing a vertical transition between the vertically adjacent structural levels, the method further comprising:
   engaging the follower on the one or more ramps and thereby transitioning the follower between vertically adjacent structural levels of the plurality of structural levels; and
   moving the indicator mount and the indicator shaft vertically along the longitudinal axis and toward the indicator aperture as the follower engages the one or more ramps.

19. The method of claim 18, wherein the indicator assembly further includes a cutout defined in the capstan assembly and extending to a bottom-most structural level of the plurality of structural levels, and a coil spring extending about the indicator shaft, the method further comprising:
   rotating the capstan assembly in a manner different from the predetermined rotational sequence;
   encountering the cutout with the follower as the capstan assembly is rotated in the manner different from the predetermined rotational sequence; and
   returning the follower to the bottom-most structural level as the follower falls into the cutout.

20. The method of claim 18, wherein at least one of the one or more ramps comprises a living hinge, the method further comprising:
   allowing the follower to traverse under the at least one of the one or more ramps when the capstan assembly is rotated in a first angular direction; and
   allowing the follower to engage and ride up the at least one of the one or more ramps when the capstan assembly is rotated in a second angular direction opposite the first angular direction.

21. The method of claim 16, wherein the indicator assembly further includes an arm extending from the indicator mount, and a follower extending from an end of the arm, and wherein the capstan assembly includes a plurality of disc keys and coaxially aligned with a central axis of the capstan assembly, each disc key defining a slot, the method further comprising:
rotating the capstan assembly in the predetermined rotational sequence with the drive input;
aligning the slot of each disc key with vertically adjacent slots and thereby forming a channel in the capstan assembly; and
biasing the follower into the channel with the arm once the channel is formed.

22. The method of claim 21, wherein the indicator shaft is releasably coupled to the indicator mount as the indicator mount rotates about the longitudinal axis, the method further comprising urging the indicator shaft vertically along the longitudinal axis with a coil spring when the indicator shaft is released from the indicator mount.

23. The method of claim 15, wherein the capstan assembly further includes a central shaft extending from the drive input, a torsion spring extending about the central shaft, and a receptacle provided at the upper end and defining a central aperture sized to releasably receive a portion of the indicator mount, the method further comprising:
resisting rotation of the central shaft with the torsion spring; and
operating the drive input to overcome a spring force of the torsion spring and thereby releasing the indicator mount and the indicator shaft from the receptacle.

24. The method of claim 23, wherein the receptacle defines a release notch and the indicator mount provides a release member alignable with the release notch, the method further comprising:
rotating the central shaft and thereby aligning the release notch with the release member;
releasing the indicator mount and the indicator shaft from the receptacle once the release notch aligns with the release member; and
moving the indicator mount and the indicator shaft vertically along the longitudinal axis with a coil spring when the release notch aligns with the release member.

25. The method of claim 15, wherein the capstan assembly further includes a drive gear arranged to drive a driven gear positioned within the drive housing, and wherein determining that the useful life of the surgical tool has been exhausted is preceded by:
rotating the drive input and thereby driving the driven gear with the drive gear; and
performing a secondary function of the surgical tool as the driven gear is rotated with the drive gear.

* * * * *